United States Patent
Kadlec et al.

(10) Patent No.: US 12,357,479 B2
(45) Date of Patent: Jul. 15, 2025

(54) INTRALUMINAL STENT WITH HANDLE FOR TREATING BENIGN PROSTATIC HYPERPLASIA

(71) Applicant: RIVERMARK MEDICAL, INC., Milwaukee, WI (US)

(72) Inventors: Adam Kadlec, Milwaukee, WI (US); Anand Doraiswamy, Oakland, CA (US); Andrew Schieber, North Tustin, CA (US); Marcus Souza, Costa Mesa, CA (US); Nathan Chu, Irvine, CA (US)

(73) Assignee: RIVERMARK MEDICAL, INC., Milwaukee, WI (US)

( * ) Notice: Subject to any disclaimer, the term of this patent is extended or adjusted under 35 U.S.C. 154(b) by 0 days.

(21) Appl. No.: 18/513,366

(22) Filed: Nov. 17, 2023

(65) Prior Publication Data
US 2024/0115405 A1   Apr. 11, 2024

Related U.S. Application Data

(63) Continuation of application No. PCT/US2023/074925, filed on Sep. 22, 2023.
(Continued)

(51) Int. Cl.
*A61F 2/82* (2013.01)
*A61F 2/04* (2013.01)
*A61F 2/95* (2013.01)

(52) U.S. Cl.
CPC .......... *A61F 2/82* (2013.01); *A61F 2002/047* (2013.01); *A61F 2002/048* (2013.01); *A61F 2002/9528* (2013.01); *A61F 2002/9534* (2013.01)

(58) Field of Classification Search
CPC .......... A61F 2002/047; A61F 2002/048; A61F 2/95; A61F 2/82; A61F 2002/9528;
(Continued)

(56) References Cited

U.S. PATENT DOCUMENTS 5,059,169 A   10/1991   Zilber
5,064,435 A   11/1991   Porter
(Continued)

FOREIGN PATENT DOCUMENTS

CN   106901880         6/2017
CN   11023673   *   9/2019   ............... A61F 2/07
(Continued)

OTHER PUBLICATIONS

International Search Report and Written Opinion for PCT/US2019/036162, mailed Sep. 18, 2019 in 19 pages.
(Continued)

*Primary Examiner* — Seema Mathew
(74) *Attorney, Agent, or Firm* — KNOBBE MARTENS OLSON & BEAR LLP

(57) ABSTRACT

A stent is disclosed that is configured to maintain patency of the prostatic urethra despite an enlarged prostate. The stent can include a handle that, in an undeflected position, is disposed outside of the flow path of the stent. When the handle is pulled, the handle can deflect to generally aligned with a central axis of the stent. A capture device is disclosed that includes a tapered tip to navigate a working channel of a delivery device and a hook that can capture the stent handle and be moved into a tube to retain the stent handle to facilitate maneuvering of the stent in and out of the working channel of the delivery device. A loading adapter with a tapered port is disclosed that can be disposed on the delivery device to distribute compressive forces applied by the port on the stent during loading into the working channel.

22 Claims, 25 Drawing Sheets

Related U.S. Application Data

(60) Provisional application No. 63/484,462, filed on Feb. 10, 2023, provisional application No. 63/376,984, filed on Sep. 23, 2022.

(58) Field of Classification Search
CPC .......... A61F 2/04; A61F 2/9517; A61F 2/966; A61F 2/86; A61F 2002/9534; A61F 2002/9665; A61F 2220/0008; A61F 2/07; A61F 2002/9511; A61F 2/2418; A61F 2/9522; A61M 27/008; A61M 25/0017
See application file for complete search history.

(56) References Cited

U.S. PATENT DOCUMENTS

| | | | |
|---|---|---|---|
| 5,246,445 A | 9/1993 | Yachia et al. | |
| 5,466,242 A | 11/1995 | Mori | |
| 5,496,365 A * | 3/1996 | Sgro | A61F 2/915 |
| | | | 623/1.2 |
| 5,667,486 A * | 9/1997 | Mikulich | A61F 2/04 |
| | | | 604/8 |
| 5,735,871 A * | 4/1998 | Sgro | A61F 2/82 |
| | | | 606/198 |
| 6,019,779 A | 2/2000 | Thorud et al. | |
| 6,022,312 A | 2/2000 | Chaussy et al. | |
| 6,139,536 A | 10/2000 | Mikus et al. | |
| 6,183,507 B1 | 2/2001 | Lashinski et al. | |
| 6,305,436 B1 | 10/2001 | Andersen et al. | |
| 6,315,791 B1 | 11/2001 | Gingras et al. | |
| 6,436,133 B1 | 8/2002 | Furst et al. | |
| 6,494,908 B1 | 12/2002 | Huxel et al. | |
| 6,702,846 B2 | 3/2004 | Mikus et al. | |
| 6,733,536 B1 | 5/2004 | Gellman | |
| 6,852,124 B2 | 2/2005 | Cox et al. | |
| 6,911,041 B1 | 5/2005 | Zscheeg | |
| 7,112,226 B2 | 9/2006 | Gellman | |
| 7,169,187 B2 | 1/2007 | Datta et al. | |
| 7,485,130 B2 | 2/2009 | St. Germain | |
| 7,527,651 B2 | 5/2009 | Gellman | |
| 7,780,719 B2 | 8/2010 | Killion et al. | |
| 7,935,142 B2 | 5/2011 | Gregorich | |
| 7,993,387 B2 | 8/2011 | Clerc et al. | |
| 8,287,602 B2 | 10/2012 | Daignault et al. | |
| 8,357,179 B2 | 1/2013 | Grandfield et al. | |
| 8,465,551 B1 | 6/2013 | Wijay et al. | |
| 8,506,619 B2 | 8/2013 | Ortiz et al. | |
| 8,512,392 B2 | 8/2013 | Bidne et al. | |
| 8,529,596 B2 * | 9/2013 | Grandfield | A61B 17/320725 |
| | | | 606/127 |
| 8,591,569 B2 | 11/2013 | Shin et al. | |
| 8,603,187 B2 | 12/2013 | Kilemnick et al. | |
| 8,709,060 B2 | 4/2014 | Osborne | |
| 8,795,345 B2 * | 8/2014 | Grandfield | A61F 2/90 |
| | | | 623/1.1 |
| 9,044,263 B2 | 6/2015 | Grandfield et al. | |
| 9,072,537 B2 * | 7/2015 | Grandfield | A61B 17/221 |
| 9,138,336 B2 | 9/2015 | Carman et al. | |
| 9,307,996 B2 | 4/2016 | Johnson et al. | |
| 9,549,739 B2 | 1/2017 | Catanese, III et al. | |
| 9,603,733 B2 * | 3/2017 | Shobayashi | A61F 2/966 |
| 9,848,905 B2 | 12/2017 | Kilemnik | |
| 10,035,005 B2 | 7/2018 | Bar-On et al. | |
| 10,105,132 B2 | 10/2018 | Lamson et al. | |
| 10,195,014 B2 | 2/2019 | Lamson et al. | |
| 10,271,977 B2 | 4/2019 | Longo et al. | |
| 10,406,333 B2 | 9/2019 | Feld | |
| 10,441,447 B2 | 10/2019 | Krieger et al. | |
| 10,478,283 B2 | 11/2019 | Bachar | |
| 10,492,792 B2 | 12/2019 | Catanese, III et al. | |
| 10,507,122 B2 * | 12/2019 | Bachar | A61F 2/04 |
| 10,555,802 B1 | 2/2020 | Shadduck | |
| 10,660,772 B2 | 5/2020 | Schwartz et al. | |
| 10,682,245 B2 | 6/2020 | Harkin et al. | |
| 10,828,184 B1 | 11/2020 | Schwartz | |
| 10,881,539 B2 | 1/2021 | Harkin et al. | |
| 10,912,637 B2 | 2/2021 | Lamson et al. | |
| 10,932,927 B2 | 3/2021 | Clinger et al. | |
| 10,952,885 B2 | 3/2021 | Sicotte et al. | |
| 10,966,813 B2 | 4/2021 | Shadduck | |
| 11,027,106 B2 | 6/2021 | Bachar | |
| 11,058,444 B2 * | 7/2021 | Girdhar | A61B 17/221 |
| 11,096,774 B2 | 8/2021 | Sicotte et al. | |
| 11,273,025 B2 | 3/2022 | Ghriallais et al. | |
| 11,285,027 B1 * | 3/2022 | Chanduszko | A61F 2/01 |
| 11,304,724 B2 * | 4/2022 | Kilemnik | A61F 2/04 |
| 11,471,148 B2 | 10/2022 | Lamson et al. | |
| 11,484,398 B2 | 11/2022 | Ghriallais et al. | |
| 11,497,637 B2 | 11/2022 | Huang et al. | |
| 11,571,290 B2 | 2/2023 | Bachar | |
| 11,602,621 B2 | 3/2023 | Ghriallais et al. | |
| 2002/0099438 A1 | 7/2002 | Furst | |
| 2002/0161427 A1 | 10/2002 | Rabkin et al. | |
| 2003/0040803 A1 | 2/2003 | Rioux et al. | |
| 2004/0102833 A1 | 5/2004 | Girton et al. | |
| 2006/0004436 A1 | 1/2006 | Amarant et al. | |
| 2006/0122693 A1 * | 6/2006 | Biadillah | A61F 2/2418 |
| | | | 427/2.25 |
| 2006/0142849 A1 | 6/2006 | Killion et al. | |
| 2006/0276871 A1 | 12/2006 | Lamson et al. | |
| 2007/0173921 A1 | 7/2007 | Wholey et al. | |
| 2009/0105719 A1 | 4/2009 | Honey et al. | |
| 2009/0149935 A1 | 6/2009 | Chu et al. | |
| 2009/0210045 A1 | 8/2009 | Sorensen et al. | |
| 2010/0130815 A1 | 5/2010 | Gross et al. | |
| 2011/0098825 A1 | 4/2011 | Shin et al. | |
| 2011/0106234 A1 * | 5/2011 | Grandt | A61F 2/86 |
| | | | 623/1.11 |
| 2011/0270276 A1 * | 11/2011 | Rothstein | A61B 17/0401 |
| | | | 606/143 |
| 2011/0276038 A1 | 11/2011 | McIntyre et al. | |
| 2012/0158155 A1 * | 6/2012 | Shin | A61F 2/04 |
| | | | 623/23.66 |
| 2012/0271405 A1 | 10/2012 | Soletti et al. | |
| 2013/0144372 A1 * | 6/2013 | Wood | D04C 1/06 |
| | | | 623/1.11 |
| 2013/0325141 A1 | 12/2013 | Gill et al. | |
| 2016/0206449 A1 * | 7/2016 | Mort | A61F 2/86 |
| 2016/0242894 A1 | 8/2016 | Davis | |
| 2017/0027724 A1 * | 2/2017 | Hossainy | A61F 11/202 |
| 2017/0216062 A1 | 8/2017 | Armstrong et al. | |
| 2017/0333230 A1 * | 11/2017 | Folan | A61F 2/90 |
| 2018/0021155 A1 | 1/2018 | Hadley et al. | |
| 2018/0264226 A1 | 9/2018 | Erbey, II et al. | |
| 2018/0318114 A1 | 11/2018 | Huang et al. | |
| 2019/0038443 A1 * | 2/2019 | Sicotte | A61F 2/885 |
| 2019/0117423 A1 * | 4/2019 | Chao | A61F 2/04 |
| 2019/0224008 A1 | 7/2019 | Bressloff et al. | |
| 2020/0038213 A1 | 2/2020 | Bly et al. | |
| 2020/0323618 A1 * | 10/2020 | Bly | A61F 2/885 |
| 2020/0368008 A1 * | 11/2020 | Koroschetz | A61L 31/06 |
| 2021/0022594 A1 | 1/2021 | Jen et al. | |
| 2021/0022893 A1 * | 1/2021 | Itoi | A61F 2/86 |
| 2021/0059704 A1 | 3/2021 | Kilemnik | |
| 2021/0145617 A1 | 5/2021 | Doi | |
| 2021/0145619 A1 | 5/2021 | Bly et al. | |
| 2021/0161642 A1 | 6/2021 | Jen et al. | |
| 2021/0307942 A1 * | 10/2021 | Flora | A61F 2/88 |
| 2022/0079736 A1 | 3/2022 | Sicotte et al. | |
| 2022/0104845 A1 | 4/2022 | Golan et al. | |
| 2022/0110737 A1 * | 4/2022 | Mehta | A61F 2/95 |
| 2022/0167921 A1 | 6/2022 | Aljuri et al. | |
| 2022/0313457 A1 | 10/2022 | Brown et al. | |
| 2022/0387165 A1 * | 12/2022 | Jang | A61B 5/1079 |
| 2022/0395363 A1 | 12/2022 | Ghriallais et al. | |
| 2023/0092775 A1 | 3/2023 | Juan et al. | |
| 2023/0200972 A1 * | 6/2023 | Bachar | A61F 2/95 |
| | | | 623/23.66 |
| 2024/0108868 A1 * | 4/2024 | Brockmann | A61M 29/00 |
| 2024/0374368 A1 * | 11/2024 | Bachar | A61F 2/962 |

(56) References Cited

U.S. PATENT DOCUMENTS

FOREIGN PATENT DOCUMENTS

| | | | | |
|---|---|---|---|---|
| DE | 3417738 | 11/1985 | | |
| DE | 19653719 | 4/1998 | | |
| EP | 0566807 | 10/1993 | | |
| KR | 20130126776 A | * 11/2013 | ............... | A61F 2/82 |
| WO | WO 1997/12562 | 4/1997 | | |
| WO | WO 2005/110285 | 11/2005 | | |
| WO | WO 2007/070788 | 6/2007 | | |
| WO | WO 2009/099632 | 8/2009 | | |
| WO | WO 2011/034768 | 3/2011 | | |
| WO | WO 2019/237071 | 12/2019 | | |
| WO | WO 2022/058751 | 3/2022 | | |
| WO | WO 2023/014917 | 2/2023 | | |
| WO | WO 2024/064905 | 3/2024 | | |

OTHER PUBLICATIONS

International Preliminary Report on Patentability and Written Opinion for PCT/US2019/036162, issued Dec. 8, 2020 in 14 pages.
International Search Report and Written Opinion for PCT/US2022/039481, mailed Nov. 16, 2022 in 18 pages.
International Search Report and Written Opinion for PCT/US2023/074925, mailed Jan. 19, 2024 in 9 pages.
International Preliminary Report on Patentability for PCT/US2022/039481, issued Feb. 6, 2024 in 9 pages.

* cited by examiner

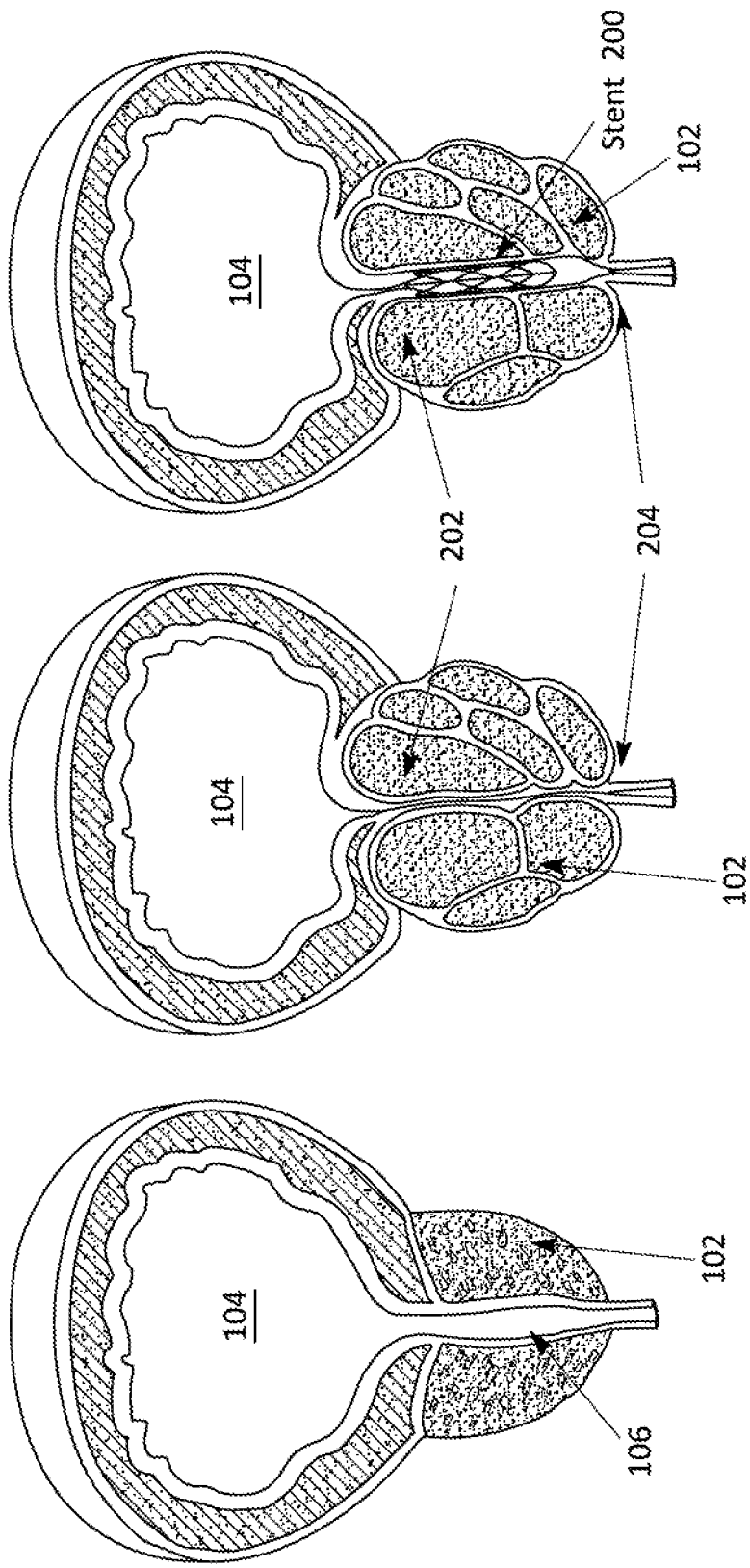

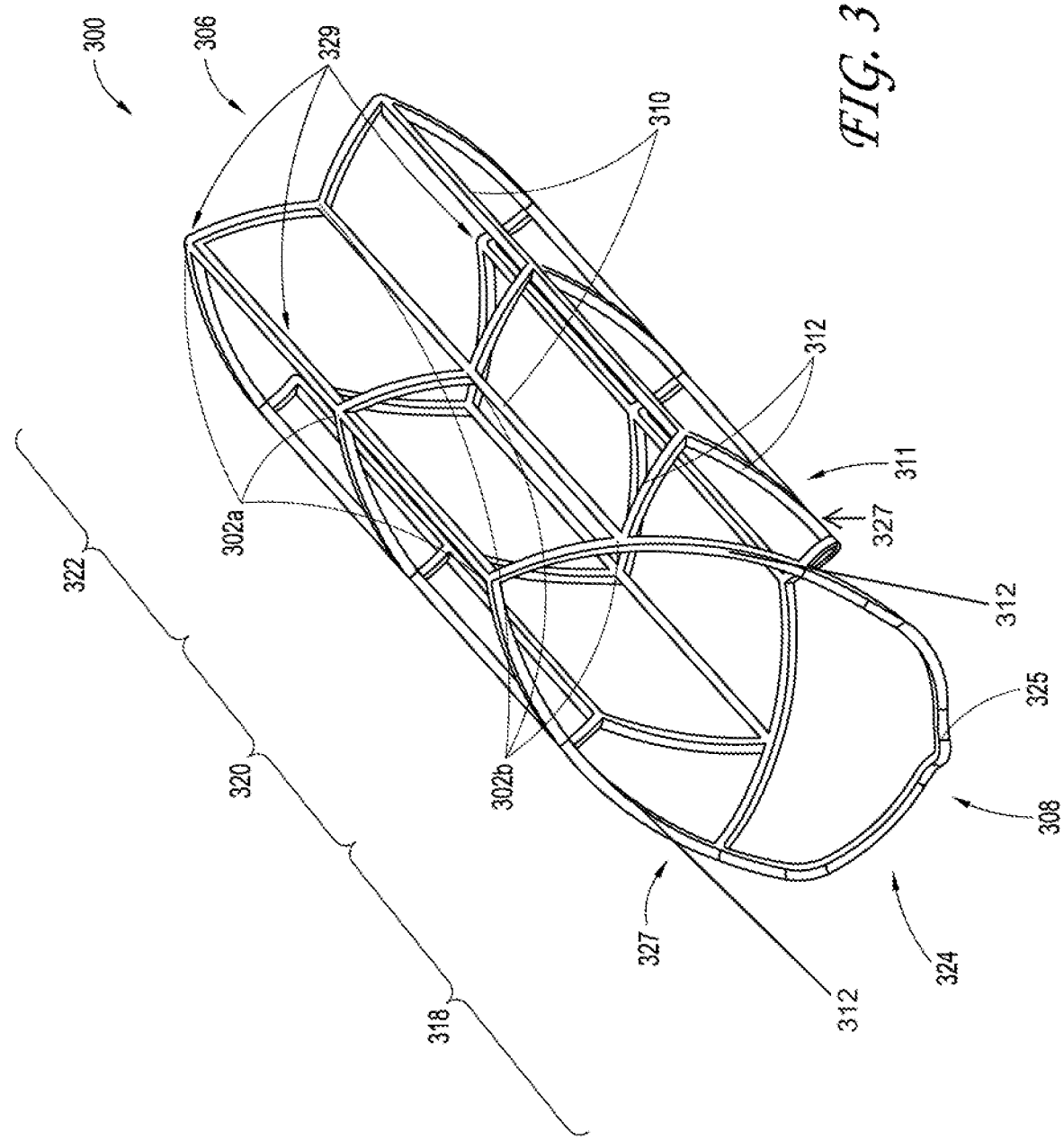

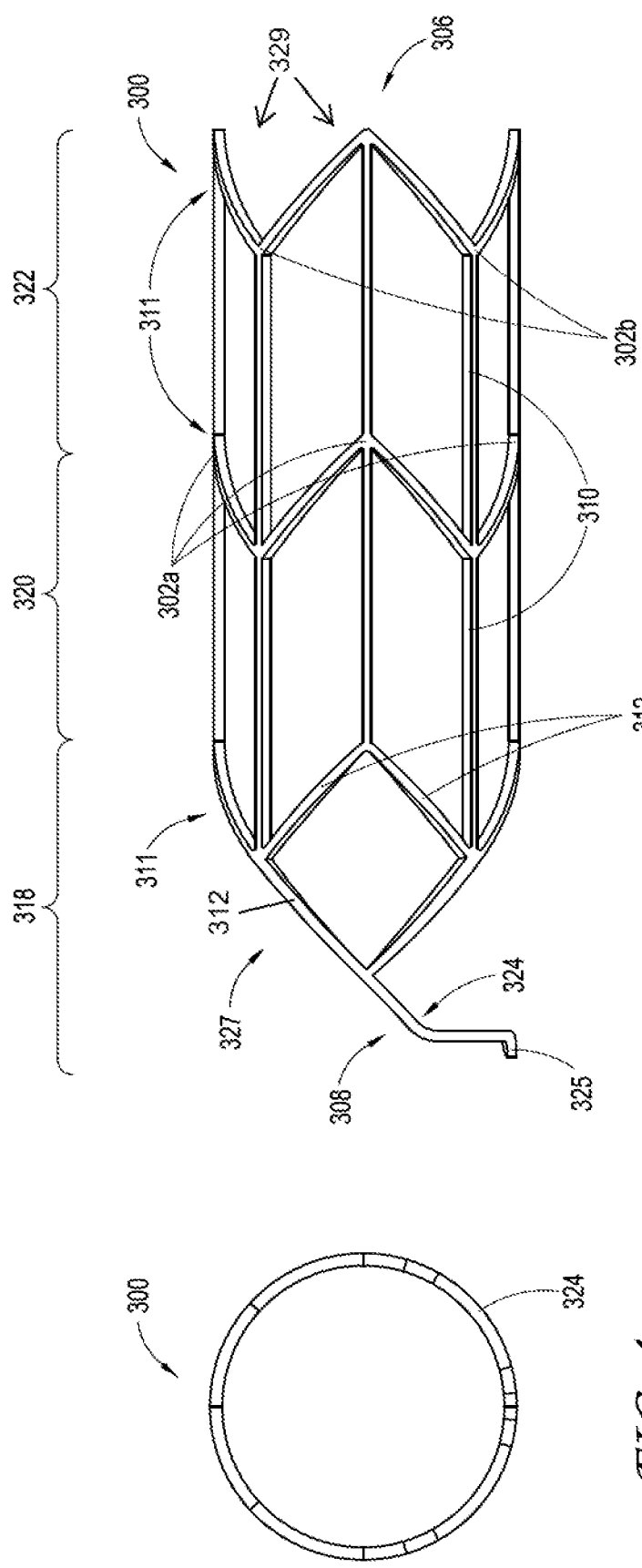

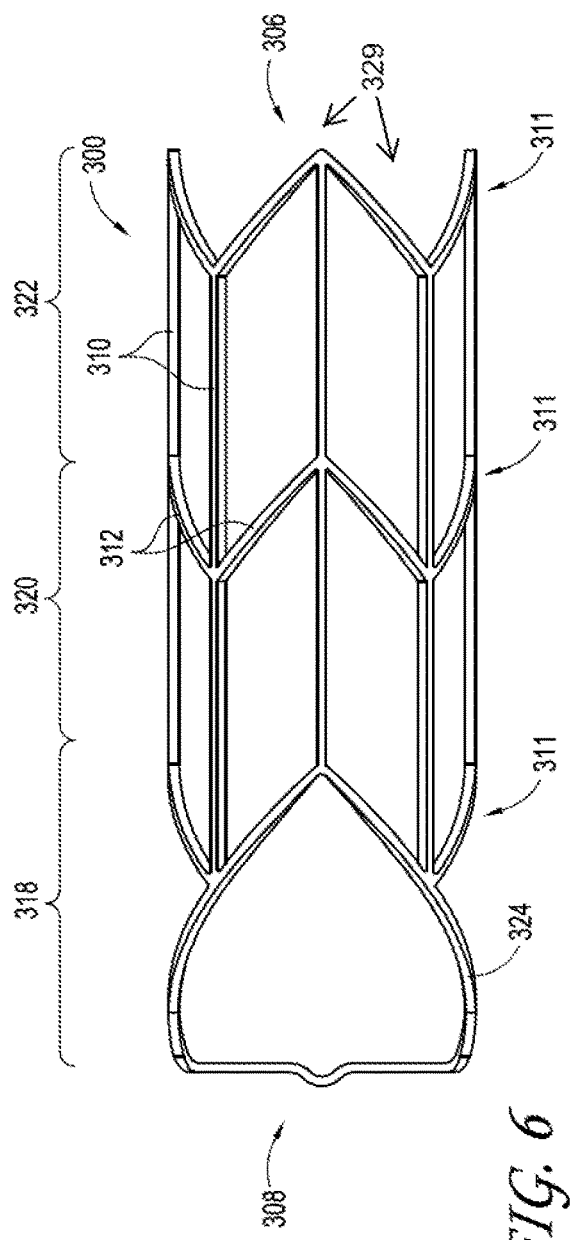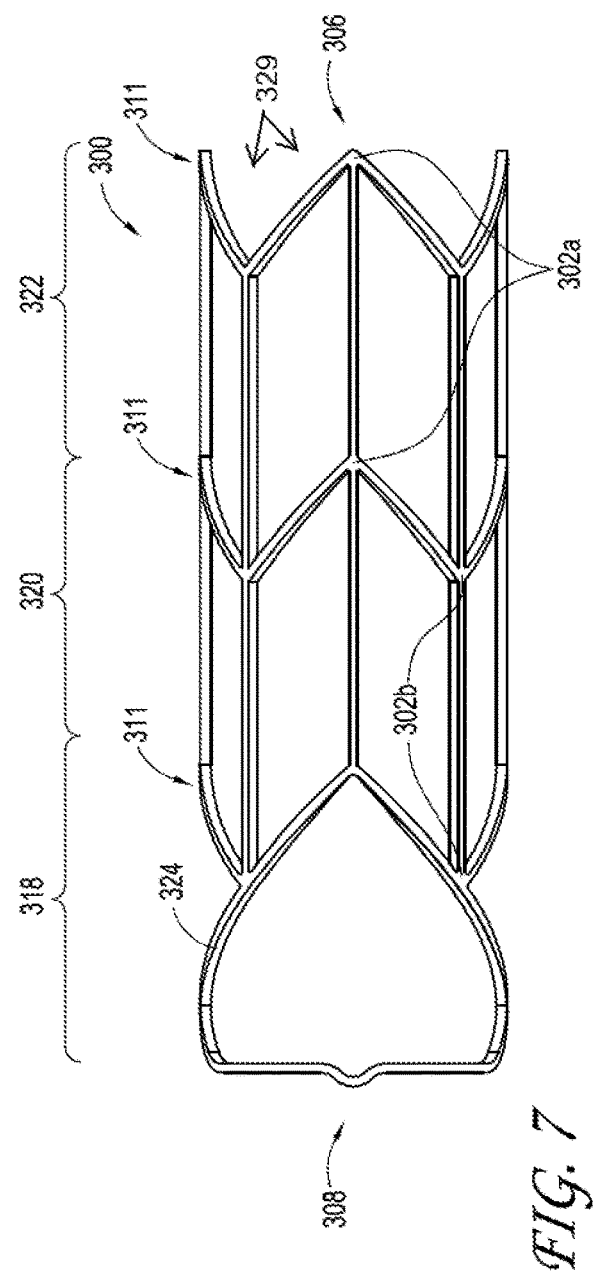

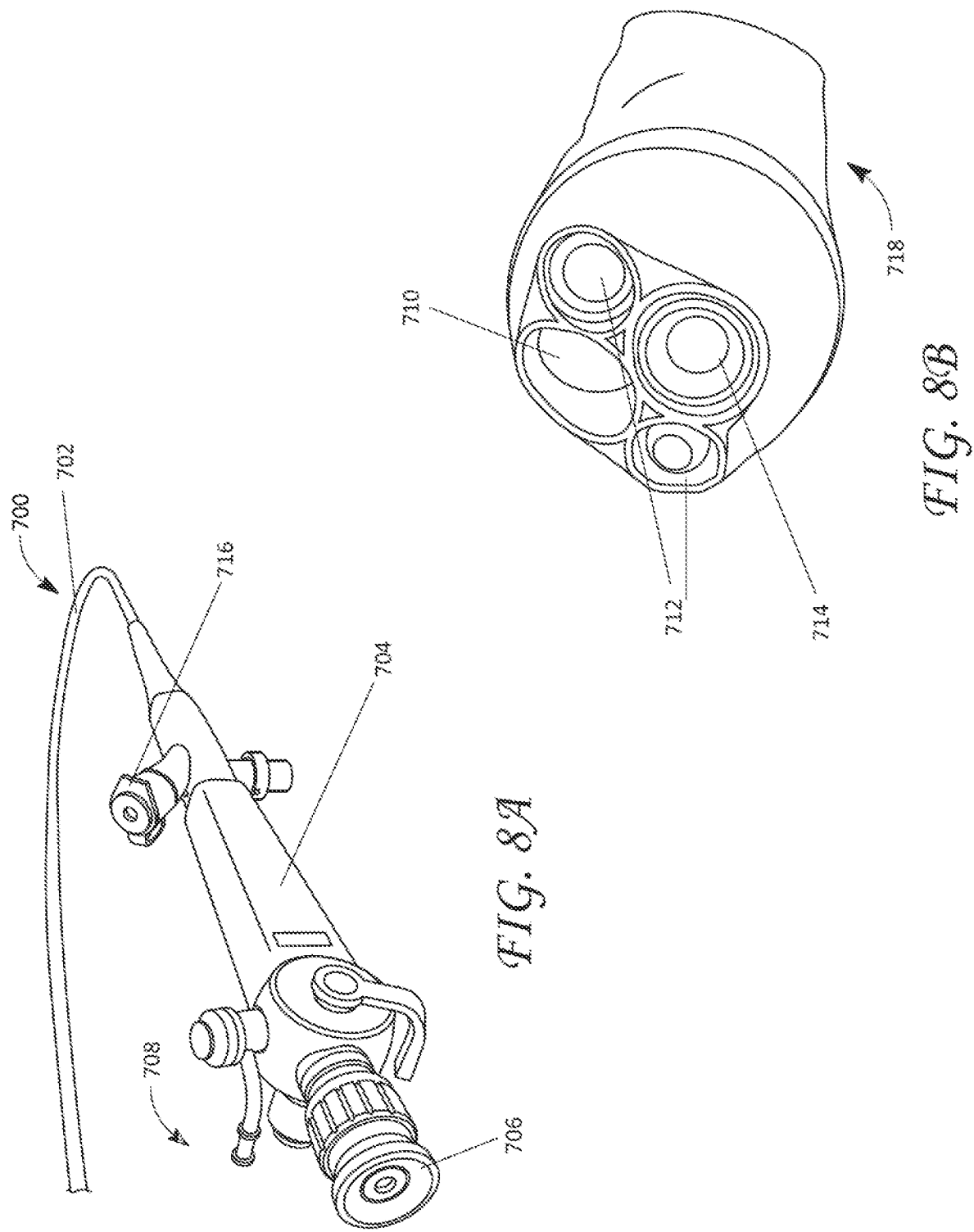

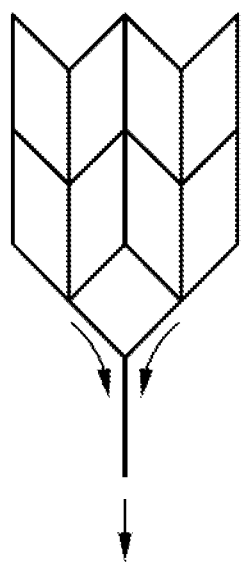
FIG. 9A
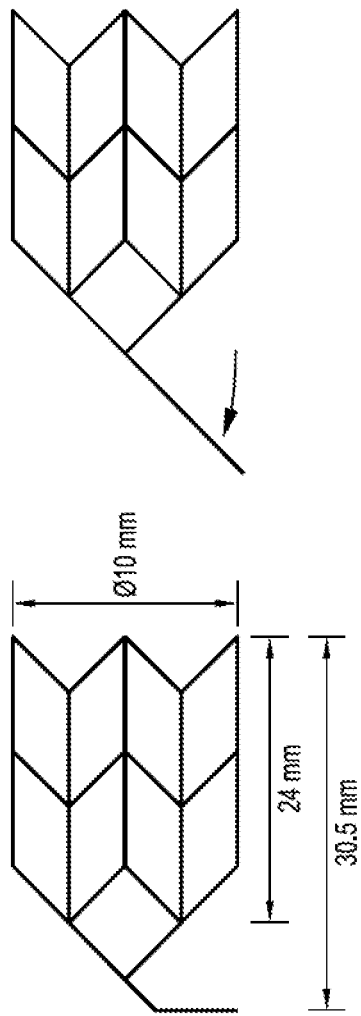
FIG. 9B
FIG. 9C
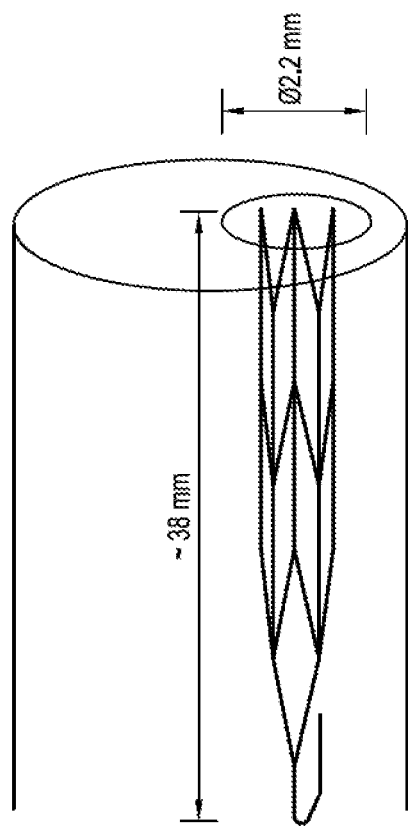
FIG. 9E
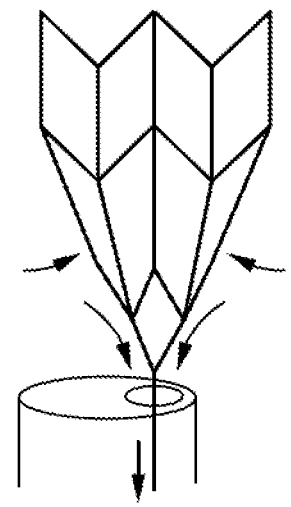
FIG. 9D

INTRALUMINAL STENT WITH HANDLE FOR TREATING BENIGN PROSTATIC HYPERPLASIA

CROSS-REFERENCE TO RELATED APPLICATION

This application is a continuation of International Application No. PCT/US2023/074925, filed Sep. 22, 2023, which claims the benefit of priority to U.S. Provisional Patent App. No. 63/484,462, filed Feb. 10, 2023, and to U.S. Provisional Patent App. No. 63/376,984, filed Sep. 23, 2022, the entire disclosures of each of which are hereby incorporated by reference.

BACKGROUND

Benign prostatic hyperplasia (BPH) is a common benign condition that develops in men and is bothersome in elderly patients. In this condition, the prostate gland is enlarged and not cancerous. Benign prostatic hyperplasia is also called benign prostatic hypertrophy or benign prostatic obstruction.

The prostate gland is a fibromuscular and glandular organ lying just inferior to the bladder. As the prostate enlarges, the gland presses against and pinches the prostatic urethra. This leads to weakening the bladder and inability to completely empty the bladder. The narrowing of the prostatic urethra causes the symptoms observed with BPH. Approximately half of all men over the age of 50 will develop an enlarged prostate. By the time men reach their 70's and 80's, approximately 85-90% of them will experience urinary symptoms from BPH.

While the etiology of BPH is not completely well-understood, it is thought to be multifactorial and endocrine controlled. BPH develops in the transitional zone of the prostatic urethra. Symptoms often include irritative and obstructive flow. Specifically, the following symptoms may be suggestive of BPH: urinary frequency, urinary urgency, trouble starting a urinary stream, retention, incontinence, nocturia, pain after ejaculation. Complications of BPH include bladder stone, urinary tract infection, hematuria, bladder decompensation, renal failure, and acute/chronic urine retention.

Pharmacologic approaches for treatment include use of alpha blockers such as phenoxybenzamine (non-selective), prazosin (short-acting), terazosin & doxazosin (long-acting), and tamsulosin, alfuzosin, and silodosin ($\alpha$1a) selective blockers. Additionally, 5$\alpha$-reductase inhibitors and combination therapies are also used. Pharmacologic approaches are inadequate in effectiveness and often used as short-term treatments. Side-effects of pharmacologic approaches include orthostatic hypotension, dizziness, tiredness, retrograde ejaculation, rhinitis, and headache.

Conventional and recent surgical therapies include transurethral resection of the prostate (TURP), transurethral incision of the prostate (TUIP), laser therapy, other forms of energy to vaporize the prostate, simple prostatectomy, prostatic stents, and office-based procedures such as prostatic urethral lift. With TURP, endoscopic electrosurgical resection is used to alleviate symptoms and improve flow rate. However, TURP requires spinal or general anesthesia and a 4-6 week recovery time with at least 24 hours of catheterization. Additionally, TURP can result in impotence, incontinence, bleeding, retrograde ejaculation, and transurethral resection (TUR) syndrome (vomiting, nausea, confusion, hypertension, etc.). Simple prostatectomy may be performed when the prostate gland is over 100 grams or when BPH occurs with a large vesical stone. With laser therapy, laser energy is used to ablate, vaporize, or enucleate the prostate, which has advantages such as minimal blood loss and the ability to be performed as an out-patient procedure. However, laser therapy may require longer post-operative catheterization time and requires high cost of laser fiber and generators. Other forms of energy including microwave, focused ultrasound, water-induced thermotherapy, electrovaporization, etc., have also been tried with variable outcomes. Transurethral balloon dilation of the prostate has also been tried in the past with poor outcomes. Prostatic stents (temporary and permanent) have also been employed in the past. Poor anchoring, migration of the stent, and difficult removal have led to poor outcomes/utilization. Recent developments include prostatic urethral lift—a technique where the prostate is tied away from the urethra. While it is minimally invasive, the procedure still has some disadvantages such as use of a temporary catheter, questionable durability of outcome, and the chance of a painful/bothersome recovery for the patient.

SUMMARY

Some embodiments disclosed herein are directed to minimally invasive systems and methods for maintaining a patency of a body lumen. One non-limiting indication is treating benign prostatic hyperplasia (BPH). The device for such treatment can include a stent that is placed within the prostatic urethra. The device can be coated with polytetrafluoroethylene (PTFE), silicone, and/or other hydrophilic and/or hydrophobic coating materials. In some embodiments, the device can be coated with one or more therapeutic agents, including drugs such as alpha-1 blockers, 5 alpha-reductase inhibitors, and/or combination therapies, such as in an extended-release coating. In some embodiments, a device is not coated with one or more therapeutic agents, such as a drug.

The stent can control and improve flow throughout the range of the urethra without interfering with the natural expansion and collapse of the urethra during evacuation. For example, a proximal region of the stent (nearest the internal urinary sphincter and bladder when implanted), sometimes referred to as the tail region, can be configured with a plurality of atraumatic ends or leaflets to anchor the stent within the prostatic urethra, and to prevent proximal migration of the stent (e.g., into or towards the bladder). A middle region of the stent, sometimes referred to as the body region, can be positioned within the prostatic urethra, between the interior and exterior urinary sphincters. A distal region of the stent (nearest the external urinary sphincter when implanted) can include diamond-shaped cells and a handle. The distal region may be configured to serve as a connection point for delivery and retrieval of the stent. For example, a detachable member, such as a clamp, hook or forceps-like grasping member may releasably attach to the handle to push the stent out of or to pull the stent into the working channel of a delivery catheter or scope (such as a cystoscope, etc.) and/or to rotate it to the desired orientation.

The stent may be constructed from any one or more of a variety of materials. For example, the stent may be constructed from shape-memory alloys (SMAs), flexible metals such as stainless steel, titanium, etc., and/or flexible polymers including shape memory polymers (SMPs). In some embodiments, the stent material may include coatings to prevent degradation and encrustation. The coating might be of hydrophobic and/or hydrophilic in nature such as silicone. In some embodiments, the coating could include PTFE or expanded polytetrafluoroethylene (ePTFE). In some embodiments, the coating can include flexible silicones, hydrogels, mucoadhesive substrate, pressure-sensitive adhesives, and/or other suitable elastomers, such as synthetic rubbers. In one or more embodiments, a coating can include a micropattern that may include and/or be formed from a biologically-derived protein structure (e.g., collagen, etc.).

In some embodiments, disclosed herein is a method of implanting the urethral stent. An image-guided flexible cystoscope or a catheter with a camera can be utilized in combination with a mechanism to deploy, retrieve, and/or reposition the stent. The stent can be loaded into the flexible cystoscope from the scope's distal (output) end.

The stent can be customized or sized for a specific patient, including age, race, demographic, predispositions, urethral dimensions, prostatic dimensions, anatomical differences, and other factors unique to the patient. For example, the length of the stent or length of each region of the stent may be selected and configured to match the patient's particular anatomical dimensions.

In some embodiments, a device can include any combination of the following features, or others as disclosed herein.

In some embodiments, the techniques described herein relate to a device for maintaining patency of a prostatic urethra, the device including: a stent including a proximal end, a distal end, a passageway between the proximal and distal ends configured to facilitate flow of body fluids therebetween, a peripheral wall disposed about the passageway including a plurality of struts and a plurality of nodes coupled to each other to form a plurality of cells, and a handle biased to a position outside of the passageway of the stent, the stent configured to expand from a compressed configuration to an expanded configuration within a bodily lumen; wherein the handle is configured to be deflected when pulled in an axial direction from the position outside of the passageway to another position in the passageway.

In some embodiments, the techniques described herein relate to a device, wherein the handle is disposed on a distal end of the stent.

In some embodiments, the techniques described herein relate to a device, wherein the handle includes a curve biasing the handle to the position outside of the passageway.

In some embodiments, the techniques described herein relate to a device, wherein the handle extends from distal struts of the plurality struts and curves to extend in a direction generally perpendicular to a central longitudinal axis of the stent.

In some embodiments, the techniques described herein relate to a device, wherein the handle includes a divot configured to engage with a capture device for loading into a working lumen of a delivery device.

In some embodiments, the techniques described herein relate to a device, wherein the divot is configured to protrude distally with the stent disposed in the bodily lumen.

In some embodiments, the techniques described herein relate to a device, wherein the divot is generally disposed along a central longitudinal plane of the stent.

In some embodiments, the techniques described herein relate to a device, wherein the handle includes a loop.

In some embodiments, the techniques described herein relate to a device, wherein the handle includes a straight portion that is generally perpendicular to a central longitudinal axis of the stent.

In some embodiments, the techniques described herein relate to a device, wherein the handle is configured to be deflected when pulled from the position outside of the passageway to generally aligned with a central longitudinal axis of the stent.

In some embodiments, the techniques described herein relate to a device, including a collapsibility gradient between the proximal end and the distal end of the stent.

In some embodiments, the techniques described herein relate to a device, wherein the plurality of struts and the plurality of nodes form circumferential rings.

In some embodiments, the techniques described herein relate to a device, wherein the circumferential rings include struts of the plurality of struts in a Z pattern.

In some embodiments, the techniques described herein relate to a device, wherein the circumferential rings include angled struts of the plurality of struts in an alternating pattern of distal-angled struts and proximal-angled struts.

In some embodiments, the techniques described herein relate to a device, wherein the circumferential rings provide different outward radial forces.

In some embodiments, the techniques described herein relate to a device, wherein a middle portion of the stent provides an outward radial force that is greater than outward radial forces provided by the distal end and proximal end.

In some embodiments, the techniques described herein relate to a device, wherein the plurality of cells include diamond-shaped cells.

In some embodiments, the techniques described herein relate to a device, wherein the diamond-shaped cells are disposed proximate the handle.

In some embodiments, the techniques described herein relate to a device and 18, wherein the diamond-shaped cells distribute tension forces on the stent to facilitate collapse of the stent.

In some embodiments, the techniques described herein relate to a device, wherein the handle is biased to a position that that is coplanar with the peripheral wall when viewed from the axial direction.

In some embodiments, the techniques described herein relate to a method of loading a stent into a working lumen of a delivery device, the method including: coupling a handle of a stent to a capture device, the handle biased to a position outside of a passageway for bodily fluids through the stent; pulling the handle with the capture device in an axial direction to deflect the handle to another position in the passageway; and retracting the stent by pulling the handle with the capture device into a working lumen of a delivery device such that the stent compresses to a diameter of the working lumen.

In some embodiments, the techniques described herein relate to a method, wherein the handle is biased to a position that that is coplanar with a peripheral wall of the stent.

In some embodiments, the techniques described herein relate to a method, wherein coupling the handle of the stent to the capture device includes capturing the handle in a hook of the capture device.

In some embodiments, the techniques described herein relate to a method of delivering a stent into a prostatic urethra, the method including: pushing, with a capture device, a handle of a stent to deploy the stent outside of a working lumen of a delivery device into a prostatic urethra; and releasing the handle of the stent from the capture device to permit the handle to spring off a central longitudinal axis of the stent to engage the wall of the urethra.

In some embodiments, the techniques described herein relate to a method, wherein the handle is configured to be disposed proximal of an apex at the verumontanum.

In some embodiments, the techniques described herein relate to a capture device configured to grasp a stent, the capture device including: a tapered tip; and a body distal of the tapered tip, the body including a hook configured to couple with a stent for maneuvering the stent.

In some embodiments, the techniques described herein relate to a capture device, wherein the hook is configured to be coupled with a stent handle of the stent.

In some embodiments, the techniques described herein relate to a capture device, further including a tube configured to be disposed over the body to secure the stent to the hook.

In some embodiments, the techniques described herein relate to a capture device, wherein the tapered tip includes a periphery that extends beyond an outer periphery of the body to expose a distal-facing surface of the tapered tip, the distal-facing surface of the tapered tip configured to engage a proximal end of the tube to secure a stent handle of the stent to the hook.

In some embodiments, the techniques described herein relate to a capture device, wherein the tapered tip includes a width that is smaller than an opening into the tube to provide lateral spaces on either side of the tapered tip for the stent handle to pass while the stent handle is secured by the hook.

In some embodiments, the techniques described herein relate to a method of capturing a handle of a stent with a capture device, the method including: advancing a capture device out of a tube to expose a hook of the capture device; positioning the handle of the stent in the hook; and retracting the capture device to contact a distal-facing surface of a tip of the capture device with a proximal end of the tube such that the hook is disposed in the tube to secure the handle.

In some embodiments, the techniques described herein relate to a method, wherein the handle, while secured to the hook in the tube, passes through lateral spaces on opposing sides of the tip of the capture device to the stent.

In some embodiments, the techniques described herein relate to a handle to control movement of a capture device to capture a stent, the handle including: a first inner space and one or more retention features disposed at an opening into the first inner space; an actuation mechanism including an actuator configured to be coupled to a capture device with a push wire and a button, the actuator configured to be disposed in the first inner space of the handle and including a second inner space and one or more locking features configured to engage the one or more retention features to impede advancement of the actuator in the first inner space, and the button configured to be disposed in the second inner space and including a body and one or more grooves; wherein the button is configured to be advanced in the second inner space of the actuator to contact an inner surface of the actuator defining the second inner space and to position the one or more grooves radially inward of the one or more locking features; wherein the button is configured to be further advanced to apply a force to the actuator, causing the one or more locking features to deflect radially inward off the one or more retention features and into the one or more grooves of the button to advance the actuator in the first inner space of the handle; and wherein advancement of the actuator in the first inner space of the handle causes the push wire to advance the capture device.

In some embodiments, the techniques described herein relate to a handle, wherein the capture device is configured to be advanced out of a tube to expose a hook retaining a stent handle, such that the stent handle is permitted to deflect out of the hook to permit delivery of the stent into a urethra.

In some embodiments, the techniques described herein relate to a handle, wherein the one or more retention features includes an angled surface.

In some embodiments, the techniques described herein relate to a handle, wherein the one or more locking features include a flared edge that is complementary to the angled surface.

In some embodiments, the techniques described herein relate to a method of controlling movement of a capture device with an actuation mechanism of a handle, the method including: advancing a button in an inner space of an actuator to contact an inner surface of the actuator and position one or more grooves of the button radially inward of one or more locking features of the actuator; applying an axial force to the button and actuator to push the one or more locking features of the actuator against one or more retention features disposed at an opening into an inner space of a handle, causing the one or more locking features to deflect off the one or more retention features and into the one or more grooves of the button; and advancing the button and actuator in the inner space of the handle to advance a push wire coupled to the actuator to advance a capture device configured to capture a stent.

In some embodiments, the techniques described herein relate to a method, wherein the one or more retention features includes an angled surface.

In some embodiments, the techniques described herein relate to a method, wherein the one or more locking features include a flared edge that is complementary to the angled surface.

In some embodiments, the techniques described herein relate to a loading adapter to facilitate loading a stent into a working channel of a delivery device, the loading adapter including: a port disposed off a central longitudinal axis of the loading adapter, wherein the port tapers to a narrower cross-section in a distal direction; and a receiving region disposed on an opposing side of the loading adapter, the receiving region configured to receive a proximal end of a delivery device to position the loading adapter on a proximal end of the delivery device; wherein the port is configured to be coaxially aligned with a working channel of the delivery device to facilitate loading the stent into the working channel.

In some embodiments, the techniques described herein relate to a loading adapter, wherein a distal side of the port includes a diameter corresponding to a diameter of the working channel.

In some embodiments, the techniques described herein relate to a loading adapter, further including a lumen with a consistent diameter connecting the port and the receiving region.

In some embodiments, the techniques described herein relate to a loading adapter, wherein the consistent diameter of the lumen corresponds to a diameter of the working lumen.

In some embodiments, the techniques described herein relate to a loading adapter, wherein the taper of the port distributes compressive forces on a stent as the stent is pulled through the port and collapses.

In some embodiments, the techniques described herein relate to a method of loading a stent in a working channel of a delivery device with a loading adapter, the method including: disposing a loading adapter over a proximal end of a delivery device; coaxially aligning a tapered port of the loading adapter with a working channel of a delivery device; pulling a stent into the tapered port such that compressive forces distributed by the tapered port compress the stent to a size to enter the working channel; and pulling the stent into the working channel.

In some embodiments, the techniques described herein relate to a method, further including rotating the loading adapter on the proximal end of the delivery device to coaxially align the tapered port with the working channel.

BRIEF DESCRIPTION OF THE DRAWINGS

FIG. 2A shows a schematic cross-section of the prostatic urethra and the bladder in the case of a healthy prostate. FIG. 2B illustrates an enlarged prostate compressing the prostatic urethra. FIG. 2C illustrates an enlarged prostate with a urethral stent positioned within the prostatic urethra to maintain the patency of the prostatic urethra.

FIG. 3 illustrates an isometric view of a urethral stent configured to be positioned within the prostatic urethra, as shown in FIG. 2C.

FIG. 4 illustrates an end view of the urethral stent of FIG. 3.

FIG. 5 illustrates a side view of the urethral stent of FIG. 3.

FIG. 6 illustrates a top view of the urethral stent of FIG. 3.

FIG. 7 illustrates a bottom view of the urethral stent of FIG. 3.

FIGS. 8A and 8B illustrate one embodiment of a delivery device (e.g., cystoscope) suitable for delivering a urethral stent, such as the urethral stent of FIG. 3-7. FIG. 8A illustrates a distal end (e.g., end disposed outside urethra during stent delivery procedure) of the delivery device. FIG. 8B illustrates a proximal end (e.g., end disposed inside urethra during procedure) of the delivery device.

FIGS. 9A-9E illustrate schematic representations of a urethral stent configured to be positioned within the prostatic urethra, and showing various states of the stent's handle (e.g., basket hook, loop, hook). FIG. 9A illustrates the stent handle in an undeflected configuration, which can include a distal end (e.g., end positioned away from the bladder) axially aligned with a peripheral wall of the stent formed by the struts. FIG. 9B illustrates the handle of the stent being pulled into the pulling configuration illustrated in FIG. 9C, which shows the handle generally aligned with a central longitudinal axis of the stent. FIG. 9D illustrates the stent being pulled at the handle into the working lumen of the delivery device, which can collapse the stent. FIG. 9E illustrates the stent disposed in the working lumen of the delivery device in a collapsed configuration.

FIG. 10A illustrates a side view of the capture device. FIG. 10B illustrates a top view of the capture device.

FIG. 11A illustrates the hook of the capture device deployed from within the tube and coupled with the stent handle. FIG. 11B illustrates the hook of the capture device retracted into the tube to secure the stent handle in the hook. FIG. 11C illustrates the retracted position of the capture device with respect to the tube (or the advanced position of the tube with respect to the capture device) of FIG. 11B from a top perspective.

FIG. 12A illustrates the capture device being navigated through a straight working lumen of a delivery device with a face plate disposed on a proximal end (e.g., end to be disposed in the urethra closest the bladder). FIGS. 12B and 12C illustrate the capture device being navigated through a working lumen of a delivery device with a turn (e.g., angle).

DETAILED DESCRIPTION

Figure 1:
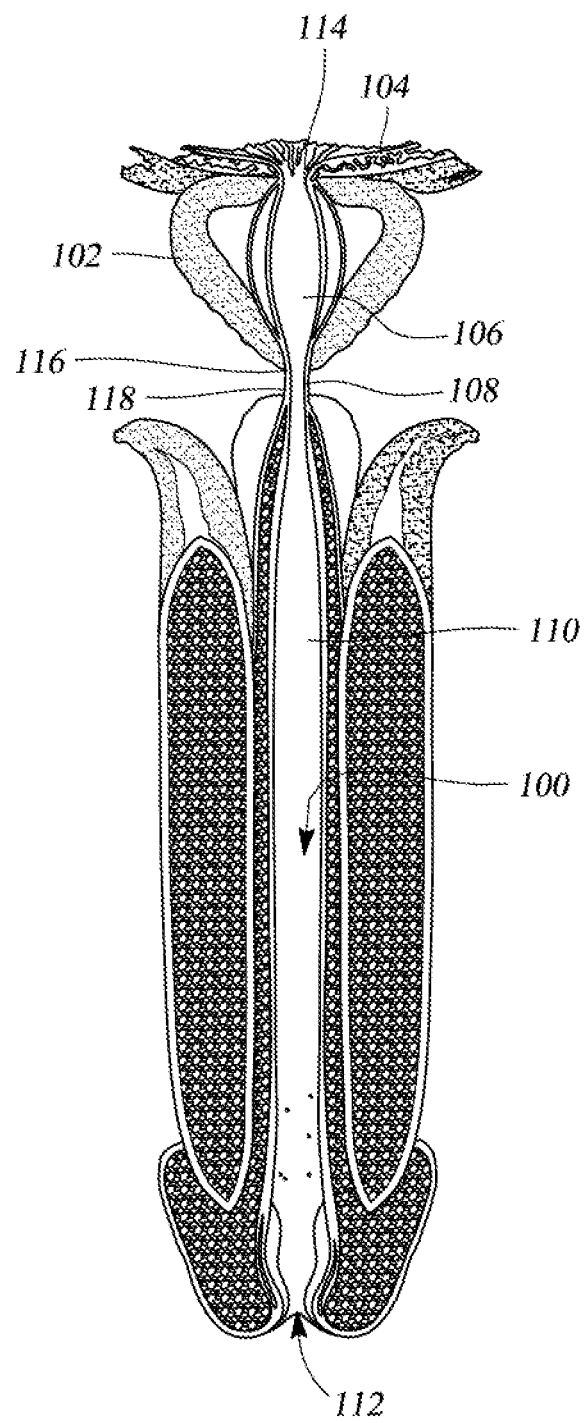
FIG. 1 illustrates a cross-sectional view of a male urethra and associated anatomy.

Several factors are considered to influence the onset and progression of Benign Prostate Hyperplasia (BPH), also known as Benign Prostate Hypertrophy. The most common factor is aging and the shift in hormonal balance. FIG. 1 illustrates the cross-section of a male urethra 100 in detail. A prostate 102 is shown right below (e.g., inferior of, distal of) a bladder 104. The region of the urethra 100 surrounded by the prostate 102 is a prostatic urethra 106, which is bounded by a bladder opening proximally and a membranous part of urethra 108 distally. Below the membranous part of the urethra 108, the urethra 100 becomes a cavernous (penile) urethra 110 and continues to and ends at an external urethral orifice 112. An internal urinary sphincter (not shown) is located at and surrounds the junction between the bladder 104 and a proximal end 114 of the prostatic urethra 106. The internal urinary sphincter (not shown) controls the flow of fluid from the bladder 104 into the prostatic urethra 106. An external urinary sphincter (not shown) is located at the membranous part of the urethra 108. The external urinary sphincter (not shown) surrounds the junction between a distal end 116 of the prostatic urethra 106 and a proximal end 118 of the penile urethra 110.

FIG. 2A illustrates the prostatic urethra 106 connected to the bladder 104 and surrounded by the prostate 102 in a normal condition. As illustrated in FIG. 2B, the prostatic urethra 106 is compressed to a reduced diameter when the prostate 102 is enlarged. This leads to the various symptoms observed in the progression of BPH, including but not limited to urinary frequency, urgency, nocturia, hesitancy, weak stream, straining, and/or prolonged voiding. An implanted device 200 for overcoming the symptoms of BPH is shown in FIG. 2C. The implanted device 200 is a urethral stent that is located entirely within the prostatic urethra 106, between the internal urinary sphincter 202 and the external urinary sphincter 204.

Disclosed herein are devices, including stents that can be configured to adjust the diameter and opening of the prostatic urethra. Prostatic urethral stents can include various generally prosthetic devices, including tubular members configured to maintain or improve the patency of at least a portion of the urethra, such as the prostatic urethra. In some embodiments, a device can improve the patency of the prostatic urethra, but not the membranous urethra or penile urethra. The stents described herein can be configured to maintain patency but not extend the urethra beyond a natural diameter.

FIG. 3 illustrates a perspective view of one such device in the form of a urethral stent 300. The urethral stent 300, or stent 300, can include a generally cylindrical shape with a plurality of nodes 302 (e.g., proximally pointing nodes 302a and/or distally pointing nodes 302b) and struts (e.g., angled struts 312 and/or longitudinal struts or bridges 310). In some embodiments, the nodes 302 and struts 310, 312 can be formed by cutting material away from a cylindrical member. In some embodiments, the nodes 302 and struts 310, 312 can be formed with additive manufacturing, casting, machining, molding, and/or using other techniques. The nodes 302 may be generally triangular or arrowhead shaped. The nodes 302 may point towards the stent's proximal end 306 or distal end 308, which can include some nodes 302 pointing toward the proximal end 306 and other nodes 302 pointing toward the distal end 308. The nodes 302 can connect longitudinal struts 310 and angled struts 312 to each other to form parallelograms, trapeziums, and/or quadrilateral-shaped cells. The angled struts 312 can vary in orientation moving circumferentially around the stent 300. For example, a forward angled strut 312 can attach to a reverse angled strut 312, and consecutively to a forward angled strut 312, which can form one or more Z-shaped rings 311 (e.g., one, two, three, four, five, six, etc.) around the stent 300 circumference. The illustrated stent 300 includes three such Z-shaped rings 311, as shown in FIG. 3, but may include more or less than three. In some embodiments, the angled struts 312 can be curved. The stent's distal end 308 can include a handle 324 (e.g., bucket handle, loop, arc). The handle 324 can extend from curved and/or angled struts 312 at a nose region 318 (e.g., leading struts, distal-most struts, distal-face struts), which can, in some embodiments, form a heart and/or shield shape, as illustrated in the top and bottom views of FIGS. 6 and 7. The handle 324 can be a continuation of the struts 312 at the nose region 318. The handle 324 can extend from one strut 312 and loop to another strut 312. The handle 324 can include a divot 325 (e.g., protrude, crimp, notch, bend, curve, contour), which can be small relative to the size of the handle 324. The divot 325 can be disposed in the middle of the handle 324, which can include being disposed on the loop of the handle halfway between the struts 312. The divot 325 can be disposed on a central longitudinal plane dividing the stent 300 into two longitudinal halves. The divot 325 can be configured to engage an engagement feature, such as a hook, of another device. The struts 310, 312 may have a width, which can be in a circumferential direction, of about 0.15 mm, 0.16 mm, 0.17 mm, 0.18 mm, 0.19 mm. 0.20 mm, 0.21 mm, 0.22 mm, 0.23 mm, 0.24 mm, and/or 0.25 mm. The struts 310, 312 and/or nodes 302 may have a thickness, which can be in a radial direction, of about 0.20 mm, 0.21 mm, 0.22 mm, 0.23 mm, 0.24 mm, 0.25 mm, 0.26 mm, 0.27 mm, 0.28 mm, 0.29 mm, and/or 0.30 mm. The struts 310, 312 and nodes 302 may form a peripheral wall of the stent 300, which can have the foregoing thicknesses (e.g., uniform thickness). The width of the struts 310, 312 in the circumferential direction can be smaller than a thickness of the struts 310, 312 and/or nodes 302. The width of the struts 310, 312 in the circumferential direction can be smaller than a thickness of the peripheral wall (e.g., struts 310, 312 and nodes 302) of the stent 300 in the radial direction. The stent 300 can be electropolished.

A longitudinal strut 310 can connect to an angled strut 312 to form an acute angle and another angle that is supplementary to the acute angle. The acute angles formed between longitudinal struts 310 and the angled struts 312 of a particular cell may be equal or decrease in magnitude moving from cell to cell in the proximal direction. For example, the acute angles formed between the longitudinal struts 310 and the angled struts 312 of a cell in the stent's body region 320 may be larger than the acute angles formed between the longitudinal and angled struts of the cells in the stent's tail region 322, which can configure the stent 300 to be stiffer (e.g., apply a larger radial force) in the body region 320 compared to the tail region 322. In some embodiments, the longitudinal lengths of the cells increase moving along the longitudinal axis of the stent 300 in the proximal direction (towards the stent's proximal end 306). In some embodiments, the acute angles are equal and do not change from cell to cell.

Adjacent circumferentially positioned cells can form longitudinal regions of the urethral stent 300. For example, the illustrated stent of FIG. 3 can include nose, body, and tail regions 318, 320, 322. Each region 318, 320, 322 can be configured for a particular clinical and anatomical function, as described herein.

The nose region 318 of the stent 300 is located at the stent's distal end 308. The struts 331 at the nose region 318 are formed into the handle 324. The handle 324 may be used to attach to a deployment and/or retrieval member (not shown) that may be used to manipulate (e.g., advance, retract, rotate, etc.) the stent 300, which can include pushing and/or pulling the stent 300 into and/or out of the working lumen of a deployment device. Pulling on the handle 324 (in the distal direction, away from the bladder when implanted) can cause a lever action of the handle 324 and compression of the stent 300 into a collapsed position so it may be drawn into the working channel of a deployment device (e.g., a catheter, cystoscope, etc.), as will be further described subsequently. The parallelogrammatic or quadrilateral cell shapes and the angular structures formed by the angular struts 312 facilitate easier collapse of the stent 300. The divot 325 of the handle 324 can provide an coupling (e.g., attachment) point and/or region for coupling (e.g., engaging) with another device (e.g., capture device, deployment device), which can facilitate pulling or pushing forces applied at the divot 325 being evenly and symmetrically distributed to the stent 300. This geometry can facilitate smooth, symmetric collapse and/or expansion of the stent 300 during loading for deployment into a cystoscope, deployment, and/or retrieval, as will be discussed herein.

The nose region 318 can include two diamond-shaped cells 327 formed from distally located, angled struts 312. The diamond-shaped cells 327 help control the distribution of tension forces applied to the stent 300 and the handle 324 to further assure a smooth collapse and expansion of the stent 300 during loading, deployment, and/or retrieval.

The nose region 318 of the stent 300 can enable a clinician to rotationally orient the stent 300 about its longitudinal axis. The shape of the handle 324 can enable a clinician to orient the stent 300 with respect to the anatomy of the patient's urethra 100. The handle 324 can be configured to position the divot 325 on a projected annular plane of the peripheral wall (e.g., peripheral wall of the of the stent 300. The divot 325 can be axially aligned with a longitudinal strut 310.

In some embodiments, the outward radial force provided by the stent 300 generally decreases along the stent's proximal direction. The urethral stent 300 may be more collapsible in the proximal direction of the stent 300 (towards the bladder, when implanted). For example, the stent 300 may be characterized by a collapsibility gradient. The body region 320 of the stent 300 may provide the greatest radial force and, therefore, the least collapsibility when implanted within the prostatic urethra 108. The tail region 322 of the stent 300 may provide the least radial force and, therefore, the greatest collapsibility when implanted within the prostatic urethra 108. In other embodiments, the outward radial force provided by the stent 300 can be uniform along at least the body and tail regions 320, 322. Providing a lesser force at the most proximal region (the tail) 322 can have multiple functional benefits, which can resist migration to the bladder, ease advancement of the compressed stent 300 out of the working channel, and/or permit higher resting tone of the bladder neck and internal sphincter, which may reduce patient discomfort and/or the risk of device-related retrograde ejaculation.

The body and tail regions 320, 322 of the stent 300 can provide enough radial force to counter or partially counter compressive forces of the prostatic urethra 108 from an enlarged prostate, such as a prostate of an individual suffering from BPH. The outward radial force provided by the stent's body and tail regions 320, 322 can help the prostatic urethra 108 stay open during evacuation of the bladder. The body and tail regions 320, 322 can be configured to merely counter the compressive forces applied to the urethra from an enlarged prostate. The stent 300 can be configured such that, when fully expanded, the urethra is merely restored to the natural diameter of the urethra and not beyond. The stent 300 may not expand the diameter of the urethra larger than its natural diameter. The natural diameter of the urethra can correspond to the diameter of stent 300 without the compressive forces of the prostate acting upon the stent 300. For example, the prostatic urethra 108 may be expanded to have a diameter that matches (e.g., is equal to) the diameter of other, non-prostatic regions of the urethra, such as the cavernous or penile urethra 110. Controlling the expanded diameter of the stent 300 such that the stent 300 does not expand the urethra beyond its natural diameter can provide physiologically relevant advantages. The controlled expanded diameter can provide less pressure to the wall of the prostatic urethra 108, which in turn can reduce inflammation, fibrosis, and/or epithelialization within the prostatic urethra 108. This, in turn, may lead to shorter patient recovery times and/or better long-term tolerance of the stent.

Local compression force, as a stand-in for radial force, was applied to different sizes of stents 300, and the force required to squeeze the diameter of the stent 300 in half was measured. In some embodiments, the outward radial forces provided by the rings 311 in each section of the nose, body, and tail regions 318, 320, 322 of a large stent 300 were 2.5, 2.4, and 2.1 N, respectively. In some embodiments, the outward radial forces provided by the rings 311 in each section of the nose, body, and tail regions 318, 320, 322 of a medium stent 300 were 3.0, 2.8, and 2.5 N, respectively. In some embodiments, the outward radial forces provided by the rings 311 in each section of the body and tail regions 320, 322 of a small stent 300 were 2.2, and 1.9 N, respectively. The outward radial forces of nose, body, and tail regions of a stent 300 can at least be in the range of 1.5-3.0 N.

The tail region 322 of the stent 300 can expand outward to enable leaflets 329 formed from the nodes 302 and the angled struts 312 at the proximal end 306 to engage the soft tissue of the prostatic urethra 108 near and/or at the internal urinary sphincter 202, or the bladder neck. The proximal nodes 302 may act as atraumatic anchors that contact the wall of the prostatic urethra 108 to prevent proximal (bladder-direction) migration of the stent 300 once implanted. The stent 300 may include a plurality of such leaflets 329 (e.g., four) formed at the proximal end 306 of the stent 300. Four leaflets 329 can advantageously provide rotational stability of the stent 300 in the prostatic urethra 108 during deployment and/or retrieval by contacting the tissue of the prostatic urethra at four circumferential locations.

The stent 300 may be sized to match a patient's particular anatomy. For example, the length of the patient's prostatic urethra 108 may be determined, and then a urethral stent 300 having a length equal to or less than the prostatic urethra length may be selected. In one embodiment, the length of the stent 300 may be determined by the length of the stent's tail region 322. In other words, the stents 300 of different lengths may have the same nose and body regions 318, 320, but different tail regions 322. For example, the longer stent's tail region 322 may be formed of longer longitudinal struts 310 or it may include more cells than the shorter stent's tail region 322. The length of the stent 300 can be altered by altering (e.g., increasing or decreasing) the distance between adjacent rings 311, which can include altering a length of longitudinal struts 310. The lengthening of the stent 300 can be altered by altering (e.g., increasing or decreasing) the number of rings 311 and longitudinal struts 310 extending between those rings 311.

In addition, in some embodiments, the tail region 322 of the stent 300 may be flared to a larger diameter at its proximal end. For example, the outer and inner diameters of the proximal portion of the tail 322 may be larger than the distal portion of the tail 322. In some embodiments, the outer and inner diameters of the stent 300 increase gradually and/or uniformly along the proximal direction of the stent 300. The flared region of the stent 300 may be obtained by placing the stent 300 on a cone shaped mandrel or another device and heat setting the stent 300 to obtain the desired, flared shape.

FIG. 4 shows an end view of the stent 300. As shown, the handle 324 may not obstruct the internal space (e.g., flow path) formed by the stent 300, which may permit unobstructed flow therethrough when expanded in a urethra. The stent 300 can maintain a circular shape to enable unobstructed fluid flow therethrough when expanded in a patient's urethra. FIG. 5 shows a side view of the stent 300. From the side view, the handle 324 can a profile similar to a leg, where the foot-like divot 325 extends horizontally toward the distal end 308 (e.g., in a distal direction, which can include in a direction parallel to a central longitudinal axis of the stent 300). The leg-like strut appears to rise vertically and bend at a knee to connect to an angled strut 312 that extends to form one side of a diamond-shaped cell 327. The stent 300 may taper in diameter from at least the body 320 to the distal end 308. In some embodiments, the stent 300 may taper in diameter from the proximal end 306 to the distal end 308 (e.g., the proximal end 306 can be larger than the distal end 308, the distal end 308 can be larger than the proximal end 306). From the side view, the handle 324 can project (e.g., continue in the same direction) from the angled struts 312 of the nose 318, curve, and then extend in a direction (e.g., perpendicular, such as generally perpendicular, relative to a central longitudinal axis of the stent 300) to position the divot 325 on a projected annular plane define by the peripheral wall of the stent 300, which can include being coplanar with a projected plane of the peripheral wall of the stent 300. The handle 324 can project from two angled struts 312 disposed on opposing sides of the stent 300 and connect to form a loop at the divot 325. The curve in the 324 can bias the handle 324 to the illustrated position, with the handle 324 generally out of the flow path and/or with the divot and/or other features of the handle 324 generally disposed in the projected annular plane of the peripheral wall of the stent 300.

FIGS. 6 and 7 show top and bottom views of the stent 300, respectively. The nose region 318 of the stent 300, which includes the handle 324, can have a generally heart-like and/or shield-like shape. The heart-shaped handle 324 may aid in the collapsibility and expansion of the stent 300 within the prostatic urethra 108. As illustrated, the curve in the handle 324 can, in some variants, cease distal extension of the handle 324 until the divot 325. As illustrated, the handle 324 can extend straight (e.g., perpendicular relative to a central longitudinal axis of the stent 300) inward to form a loop, which can include connecting two halves of the handle 324 at the divot 325. The distal-most portion of the handle 324 can be generally straight (e.g., be oriented perpendicularly relative to the central longitudinal axis of the stent 300), aside from the divot 325.

FIG. 8A illustrates one example embodiment of a delivery device 700 suitable for delivering the urethral stents described herein. In the illustrated embodiment, a cystoscope is provided as the delivery device 700. The cystoscope 700 includes a catheter tube 702 that terminates distally as a handpiece 704. An eyepiece 706 is located at the handpiece's distal end 708. The catheter tube 702 includes a plurality of channels formed therein which terminate proximally at a proximal end 718. As shown in FIG. 8B, the catheter tube 702 includes a working channel 710, two illumination channels 712, and a camera channel 714, all of which extend to and are exposed at the proximal end 718 for their respective functioning. The eyepiece 706 is optically coupled to the camera 714 so that the operator may visualize the interior of the lumen into which the catheter tube 702 has been inserted. A port 716 may be fluidly coupled to the working channel 710 to provide irrigation, aspiration, access to a control wire located in the working channel 710.

FIG. 9A provides a schematic illustration of a urethral stent (e.g., stent 300) having a handle, diamond-shaped cells, and multiple Z-shaped rings formed from alternating angled struts, as described herein. In some embodiments, the expanded outer diameter of the stent can be 10 mm, the combined length of the body and tail regions can be 24 mm, and the overall length, from handle to proximal leaflets can be 30.5 mm. In some embodiments, the expanded diameter of the stent can be 8, 9, 10, 11, 12, 13, 14, 15, 16, 17, 18, 19, or 20 mm, or within a range bounded by any of the two foregoing values. In some embodiments, the expanded diameter of the stent can be less than 8 mm or greater than 20 mm. In some embodiments, the body-tail region length can be between 10 and 35 mm, and/or about 10, 12, 14, 16, 18, 20, 22, 24, 26, 28, 30, 32, 34, or 35 mm. In some embodiments the overall length of the stent can be between 15 and 45 mm, and/or about 15, 18, 21, 24, 27, 30, 33, 36, 39, 42, or 45 mm. In some embodiments, increasing the spaces between the Z-shaped rings and/or adding additional Z-shaped rings to the stent can be used to achieve different effective overall lengths of the stent.

The diameter of the stent may vary along its length, when expanded. For example, the stent may have its largest diameter in the body region, and smaller diameters in the nose and tail regions. The stent diameter may taper linearly from the largest diameter to the smaller diameters, or it may be shaped to have a bulge formed in the body region. The larger diameter/bulge can help anchor the stent within the prostatic urethra, which can include preventing antegrade and/or retrograde migration of the stent over time. In some embodiments, the stent can taper from 8 mm diameter at the distal end (nose region) to 11 mm at the central portion (body region) and then to 9 mm at the proximal end (tail region).

The stent can be formed by cutting openings in the wall of a cylindrical tube, setting the tube on a mandrel so it has the desired diameter, and then heat setting the tube to form the stent. In some embodiments, the initial cylindrical tube may be larger than the desired diameter of the stent, and the stent may be heat set to have a smaller diameter than the cylindrical tube. Alternatively, a smaller diameter cylindrical tube may be used to form the stent. The smaller diameter cylindrical tube can be initially cut to form the desired wall pattern and opening, and then the tube can be expanded over a mandrel to give the tube the desired final stent diameter. The stent can then heat set on the mandrel to set the final diameter of the stent.

The delivery device of the stent to the prostatic urethra 106 may be an instrument like the cystoscope 700, as discussed above with reference to FIGS. 8A and 8B. The working channel 710 of a cystoscope 700 is typically about 2.0-2.5 mm in diameter. Therefore, it can be advantageous to form the stent from an initial tube having an outside diameter of about 2.0 mm and then expand it and heat set it on a mandrel to the final, desired diameter. In this manner, the stent can, in some instances, more easily collapse to the small diameter (e.g., about 2.0-2.5 mm) of a cystoscope working channel 710.

FIGS. 9B-9E illustrate method steps to load a stent into a working channel of a delivery device, such as a cystoscope (e.g., the cystoscope 700). In FIGS. 9B and 9C, the handle of the stent is pulled, leveled up, and straightened toward the pulling direction. As the stent handle is pulled, the stent handle may move (e.g., deflect) from a position generally outside of the central flow path of the stent to disposed in the central flow path of the stent, which can include being disposed on the central longitudinal axis of the stent. As the stent handle is pulled, the stent handle may be moved (e.g., deflected) from an angled configuration to one a generally straight configuration (e.g., generally parallel with the central longitudinal axis of the stent) extending in the distal direction. As described herein, the curve in the handle can bias the handle to a position generally outside of the central flow path until pulled. In FIG. 9D, the handle is shown being pulled into the work channel of the cystoscope. As indicated by the laterally inwardly pointing arrows, the distal end of the stent is compressed and collapsed when entering into the work channel. As shown in FIG. 9E, in some embodiments, the stent can be configured to be compressed and fit in the working channel of the cystoscope, which can include having an outer diameter of no more than 2.2 mm (e.g., the diameter of the work channel). In some embodiments, when compressed and collapsed into the work channel of a cystoscope, the outer diameter of the stent may be no more than 2.0, 2.1, 2.2, 2.3, 2.4, or 2.5 mm. In some embodiments, when compressed, the stent can have a diameter of only 1.5, 1.6, 1.7, 1.8, 1.9, 2.0, 2.1, 2.2, 2.3, 2.4, 2.5, 3.0, 3.5, or 4 mm. Due to the diamond shape of the cells formed by the struts and/or collapsing of the angled struts, collapsing of the stent can make the stent longer, which can include becoming as long as about 38 mm, as shown in FIG. 9E.

Figure 10A:
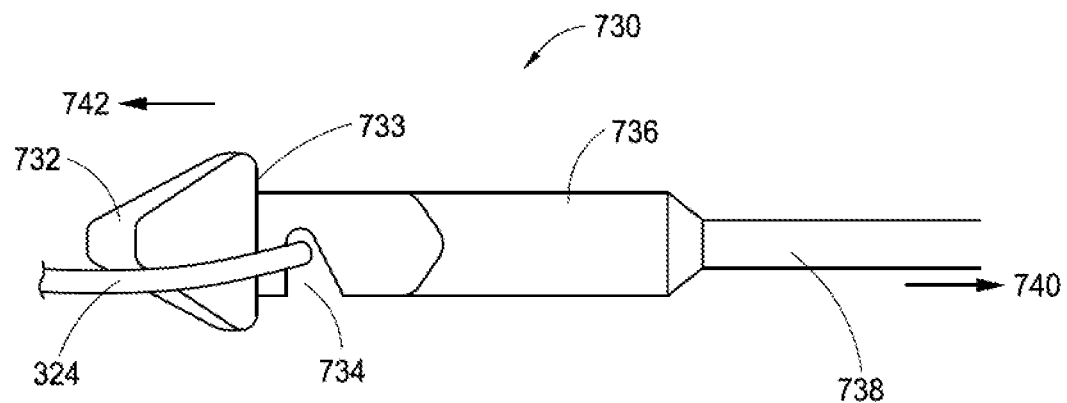
FIGS. 10A and 10B illustrate schematic representations of a capture device with a hook to capture (e.g., catch, couple with) the stent handle.
Figure 10B:
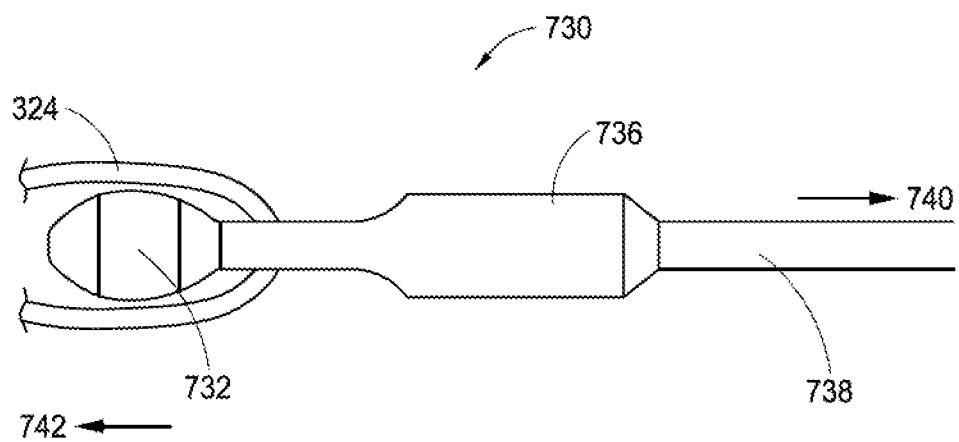

Referring to FIGS. 10A and 10B, a capture device 730 (loading device, retaining device, control device, deploy device, retrieve device) is schematically illustrated engaged with the handle 324 of the stent 300 shown in FIGS. 3-7. FIG. 10A illustrates a side view of the capture device 730 engaged with the handle 324. The capture device 730 can include a hook 734 (e.g., catch, cutout, recess, groove). The hook 734 can couple with (e.g., capture, retain, catch) the handle 324 (e.g., divot 325 of the handle 324) to maneuver the stent 300, which can include loading the stent 300 into the working channel of a delivery device, positioning the stent 300 from the working channel of a delivery device into the urethra, and/or retrieving the stent 300 from the urethra. The capture device 730 can include a body 736 (e.g., hook body, cylinder), which can include the hook 734 (e.g., the hook 734 can be formed in the body 736). The body 736 can be coupled (e.g., attached) to a push member 738 (e.g., push wire). The push wire 738 can extend in a distal direction 740, which is away from the patient being treated. The hook 734 can be a cut out formed in the body 736, capable of capturing and retaining the handle 324 of the stent 300. The capture device 730 can include a tip 732 (e.g., head, end, bullet tip, bullet head, arrow head). The tip 732 can be disposed on an end of the body 376 (e.g., proximal end). The tip 732 can extend from the body 736 in a proximal direction 742, which is oriented toward the bladder of a patient during a procedure. The tip 732 can be tapered in a distal-proximal direction. For example, when viewed from the side as in FIG. 11B, the tip 732 can widen in the distal direction 740 (e.g., away from the bladder) such that the distal portion of the tip 732 is wider than a proximal portion of the tip 732. The tip 732 can be pointed, which can include pointing in the proximal direction 742. For example, the tip 732 can include a pointed head, a bullet shaped head, arrow shaped head, and/or a cone shaped head pointed toward the proximal direction 742. When viewed from the side as in FIG. 11B, the distal portion of the tip 732 (e.g., the portion of the tip 732 disposed adjacent the body 736) can have a height larger than that of the body 736, which can expose a distal-facing surface 733 (e.g., neck edge 733) of the tip 732. The tip 732 can include rounded edges and/or corners, which can avoid tissue damage and/or the capture device 730 inadvertently catching on features of the delivery device and/or other devices. The distal-most portion of the tip 732 may, in some variants, be flat (e.g., be disposed on a plane that is generally perpendicular relative to a central longitudinal axis of the capture device 730).

FIG. 10B illustrates a top view of the capture device 730 and the stent handle 324 shown in FIG. 10A. As can be seen, the width of tip 732 can be narrower in the top view than the height of the distal portion of the tip 732 in the side view of FIG. 10A. This narrower width can provide space for the handle 324. As seen in FIG. 10B, the width of the tip 732 can vary along its length in the proximal-distal direction. The width of the tip 732 can gradually get larger in the distal direction, reach a maximum width, and then gradually get smaller in the distal direction. The tip 732 can have a width that bulges outward at a middle portion and tapers distally and proximally away from the middle portion. The tip 732 can include a larger middle portion relative to distal and proximal portions.

Figure 11A:
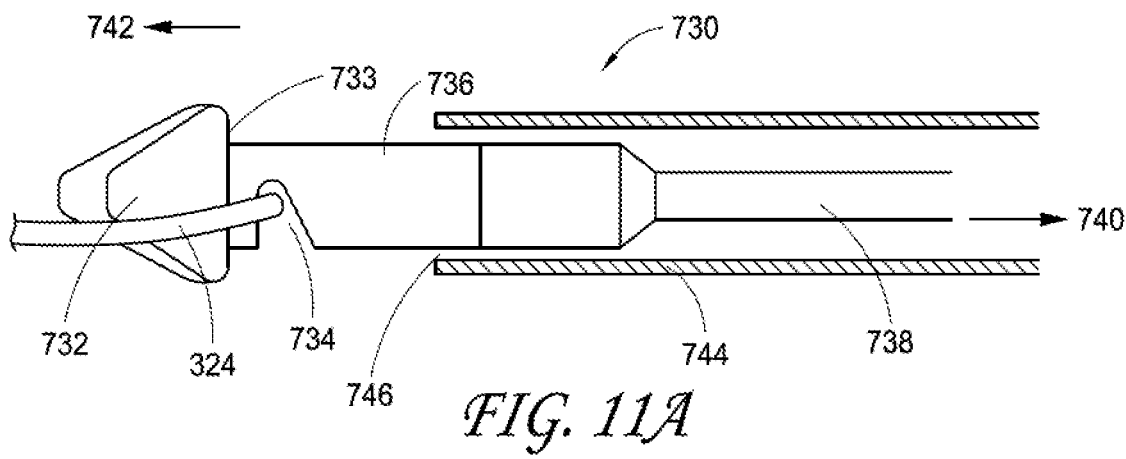
FIGS. 11A-11C illustrate schematic representations of the capture device of FIGS. 10A and 10B cooperating with a tube to securely hold and secure the stent handle to the capture device.
Figure 11B:
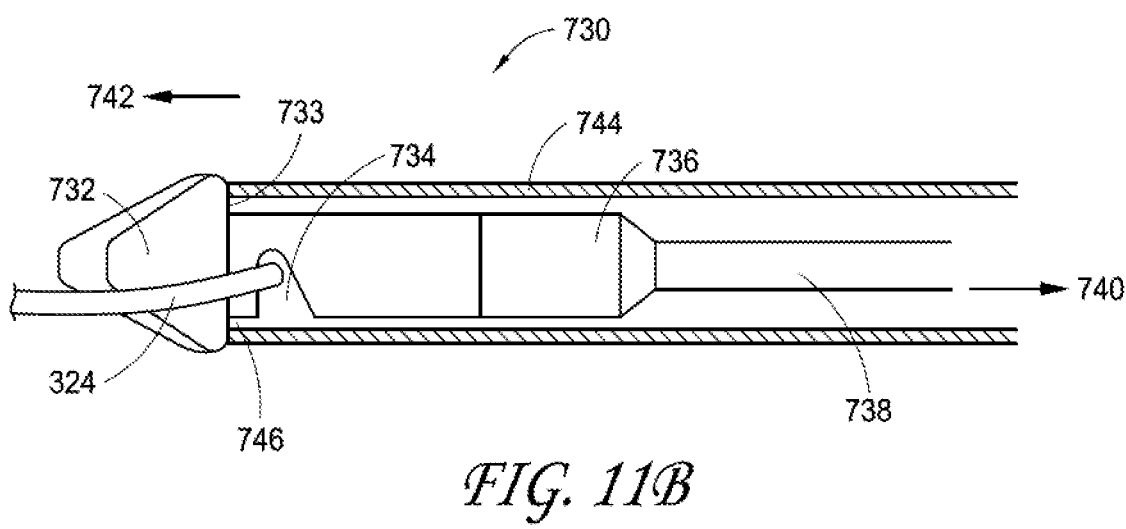
Figure 11C:
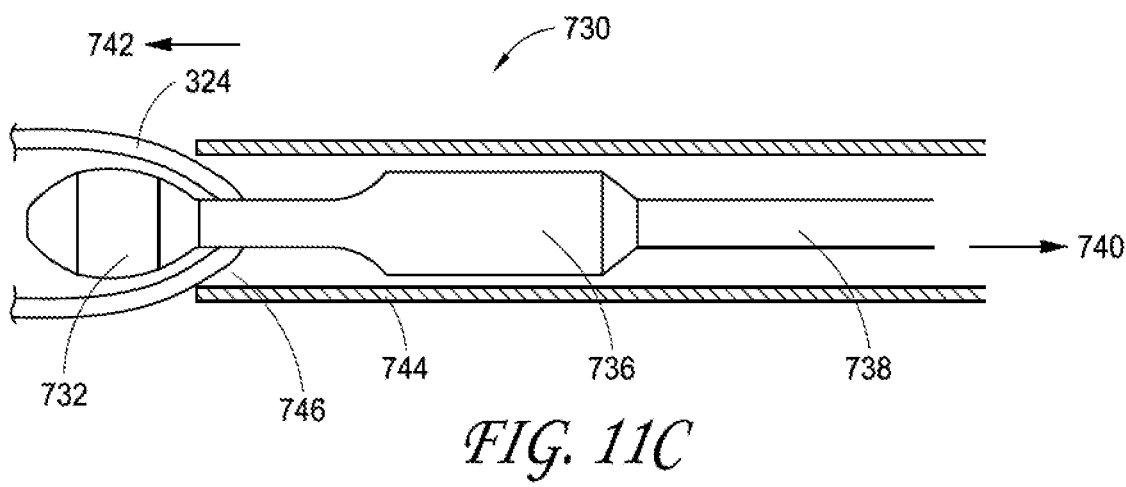

Moving to FIGS. 11A-11C, the capture device 730 is illustrated with a tube 744 (e.g., cannula). The tube 744 can be disposed over the push wire 738 and/or body 736 of the capture device 730, which can include being disposed over the hook 734. The tube 744 can include an opening 746 (e.g., proximal opening). The body 736 and push wire 738 can be maneuvered within the tube 744 to advance the capture device 730 through the opening 746 such that the hook 734 is disposed outside of the tube 744 and/or retracted through the opening 746 such that the hook 734 is disposed inside the tube 744. The push wire 738 can be rigid enough to transfer mechanical movements to the body 736. As shown in FIG. 11A, a proximal portion of the body 736 of the capture device 730 is pushed out the opening 746 to expose the hook 734. The exposed hook 734 can couple with the handle 324 of the stent 300, which can be performed outside the patient for a stent delivery procedure or inside the urethra when retrieving a previously delivered stent.

In FIG. 11B, the capture device 730 and the tubing 744 have been maneuvered with respect to each other. The body 736 has been retracted into the tubing 744 to position the hook 734 inside the tube 744. The distal-facing surface 733 can be retracted until contacting the tube 744 to prevent further retraction, which can be referred to as a closed state. In some embodiments, the push wire 738 can be pulled (e.g., pulled by a clinician at the distal end of the push wire 738) to retract the body 736 with the hook 734 into the tubing 744. With the distal-facing surface 733 contacting the proximal end of the tube 744, the stent handle 324 can be securely retained by the hook 734. In some embodiments, at this retracted (e.g., closed) state shown in FIG. 11B, the proximal end of the tubing 744 can be closely engaged with the distal-facing surface 733, leaving a small gap or no gap between them. The engagement between the tip 732 (e.g., distal-facing surface 733 of the tip 732) and the proximal surface of the tube 744 (e.g., portion of the tube 744 defining the opening 746) can secure (e.g., trap) the handle 324 on the hook 734 disposed inside the tube 744. In some embodiments, the gap between the body 736 and the tube 744 can be small enough to prevent the handle 324 from escaping the hook 734.

FIG. 11C is a top view of the retracted (e.g., closed) state engagement shown in FIG. 11B. As can be seen, the narrow width of the tip 732 can provide lateral space between the tip 732 and the wall of the tube 744 defining the opening 746 which can permit the handle 324 to pass through. The lateral sides of the tip 732 may, in some embodiments, not contact the tube 744 to provide the lateral spaces for the handle 324. For example, the tip 732 may, in some embodiments, only contact two portions (e.g., generally one hundred eighty degrees apart) of the proximal end of the tube 744 forming the opening 746. With the tip 732 engaging the tube 744, the handle can be securely retained by the hook 734. In the closed state, the hook 734 works with the tubing 744 to capture and retain the handle 324 in place. The handle 324 can be released from the hook 734 with the body 736 advanced out of the opening 746 to expose the hook 734, as shown in the deployed (e.g., open) state of FIG. 11A.

Figure 12A:
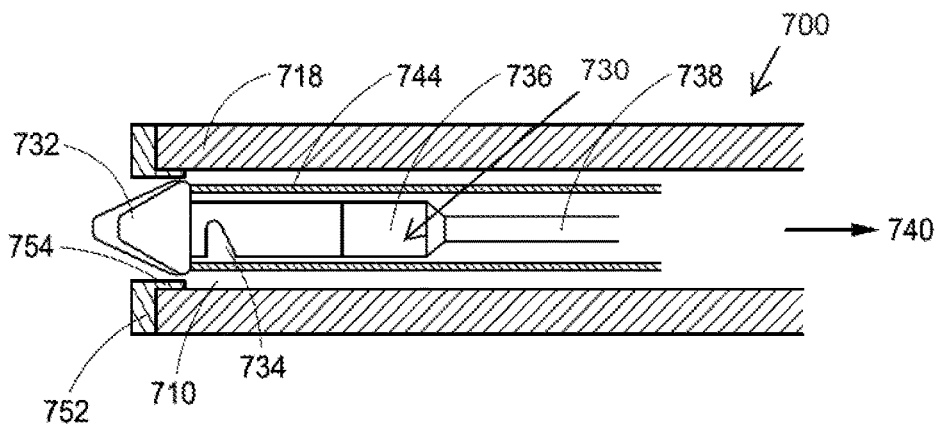
FIGS. 12A-12C illustrate schematic representations of the capture device of FIGS. 10A-11C being navigated through working lumens of delivery devices.
Figure 12B:
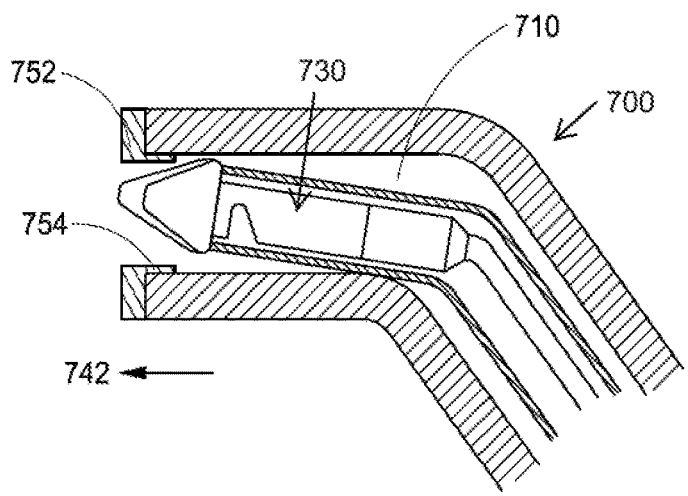
Figure 12C:
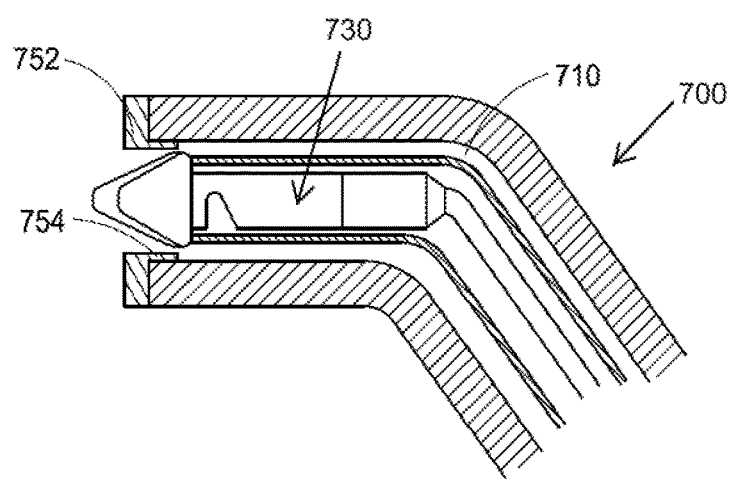

The tip 732 can provide numerous benefits, some of which are illustrated in FIGS. 12A-12C. The capture device 730 can be constructed to be compatible with most of the cystoscopes or delivery devices available on the market. For example, some cystoscopes have faceplates disposed about openings into working channels. These faceplates may be folding partially into the working channels, which may form small edges close to the exits of the work channels. FIG. 12A illustrates the load device 730 disposed inside a proximal end of a working channel 710 of a cystoscope 700 with a faceplate 752 at the opening into the work channel 710. A small edge 754 (e.g., lip) can be formed between the faceplate 752 and the inner surface of the work channel 710. The shape of the tip 732 can help reduce the risk that the capture device 730 will catch on the edge 754 of the face plate 752. For example, if the tip 732 was square and/or had sharp corners, the tip 732 may get caught at the small edge 754 or the small edge 754 may at least impose resistance to the movement of the capture device 730. The tip 732 with a pointed shape can reduce the likelihood or even prevent getting caught on the edge 754, which can be attributed, at least in part, to the proximal-most portion of the tip 732 being positioned away from the sidewall of the work channel 710 and edge 754. In some variants, the work channel 710 can include curve (e.g., bend, change in direction), which can be close to the proximal end 742. A faceplate 752 can also be attached to the proximal end of the work channel 710 of the cystoscope 700. As illustrated, the tip 732 with a pointed head can help the capture device successfully navigate through the work channel 710 and not catch on the edge 754 of the face plate 752. As shown in FIG. 12B, the flexible push wire 738 and the covering tubing 744 can bend at a location between the push wire 738 and the body 736 to enable navigating the bend of the work channel 710. As shown in FIG. 12C, the shape of the tip 732 can enable the capture device to navigate past the edge 754 and out the proximal opening of the work channel 710.

Referring to FIGS. 13A-13H, an actuation mechanism 760 is described. The actuation mechanism 760 can hold (e.g., restrain, maintain) the position of the capture device 730 relative to the tube 744, which can include holding the tip 732 against the proximal end of the tube 744 with the hook 734 in the tube 744. The actuation mechanism 760, when actuated, can advance the loading mechanism 730 relative to the tube 744 to position the hook 734 outside of the tube 744. In some embodiments, the actuation mechanism 760, when actuated, can retract the loading mechanism 730 relative to the tube 744 to position the distal-facing surface of the cap 732 against the proximal end of the tube 744 such that the hook 734 is disposed in the tube 744.

Figure 13A:
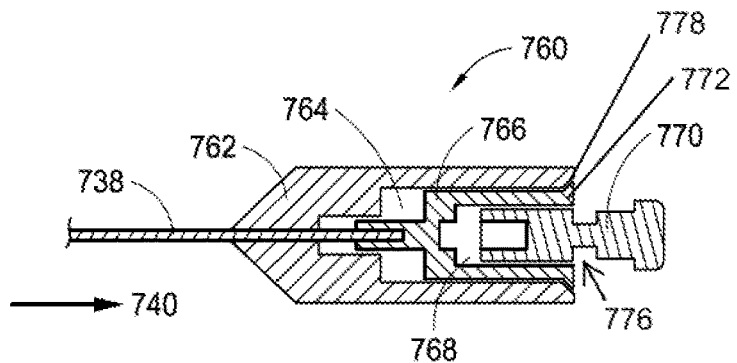
FIG. 13A illustrates a handle with an actuation mechanism to advance the capture device from the tube to deliver the stent to the prostatic urethra.
Figure 13B:
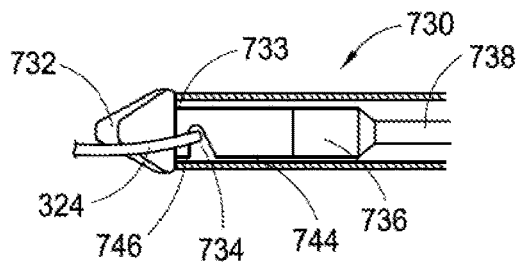
FIG. 13B illustrates the capture device that is coupled to an actuator of the handle by way of a push wire with the hook, positioned within the tube, retaining the stent handle.

As illustrated in FIG. 13A, the actuation mechanism 760 can include a handle 762 having an internal space 764 (e.g., first open ended straight inner space, cavity, pocket) that can at least partially receive (e.g., house) an actuator 766. The actuator 766 can be coupled to the push wire 738 (e.g., distal end of the push wire 738). The push wire 738 can pass through the handle 762 to extend proximally to the body 736 of the capture device 730. The actuator 766 can include an inner space 768 (e.g., second open straight opening, cavity, pocket) that can at least partially receive (e.g., house) a button 770. The outer periphery of the actuator 766 can correspond to an inner periphery of the handle 762 defining the inner space 764, which can permit the actuator 766 to translate (e.g., translate in longitudinal direction) within the inner space 764. The outer periphery of the portion of the button 770 configured to be disposed inside of the inner space 768 of the actuator 766 can correspond to an inner periphery of the actuator 766 defining the inner space 768, which can permit the button 770 to translate (e.g., translate in longitudinal direction) within the inner space 768 of the actuator 766.

The actuator 766 and handle 762 can include complementary features (e.g., surfaces) that interface (e.g., contact, engage) to prevent advancement of the actuator 766, which can prevent advancement of the push wire 738 and loading mechanism 730 relative to the tube 744 to maintain the hook 734 inside the tube 744. For example, the actuator 766 can include one or more locking features 772 (e.g., surface(s), angled surface(s), flange(s), flared edge(s), tabs(s), hook(s), beveled edge(s), lip(s)). The one or more locking features 772 can be disposed on a distal portion (e.g., distal edge) of the actuator 766, which can include being disposed at an outer periphery of the actuator 766. The one or more locking features 772 can flare radially outward relative to the longitudinal axis of the actuator. The handle 762 can include one or more retention features 778 (e.g., surface(s), angled surface(s), beveled edge(s), rim(s)). The one or more retention features 778 can be disposed at the opening into the inner space 764 of the handle 762. For example, the one or more retention features 778 can include a beveled edge at the opening into the inner space of the handle 762. The one or more locking features 772 of the actuator 766 can interface with the one or more retention features 778 of the handle 762 to prevent advancement of the actuator 766 within the inner space 764 of the handle 762, which can prevent advancement of the capture device 730 relative to the tube 744 to retain the hook 734 in the tube 744. If a proximal-direction axial force were applied to the stent 300, the engagement between the one or more locking features 772 of the actuator 766 and the one or more retention features 778 of the handle 762 can prevent advancement of the actuator 766 and corresponding proximal advancement of the push wire 738 and capture device 730 to avoid the hook 734 being advanced out of the tube 744 to permit release of the stent 300. With a proximal-direction axial force applied to the actuator 766 by way of the push wire 738, the one or more locking features 772 of the of the actuator 766 can push into the one or more retention features 778 of the handle 762, which can urge the one or more locking features 772 radially inward but the body of the button 770 can impede radially inward deflection of the one or more locking features 772. The button 770, however, can include one or more grooves 776 (e.g., recess, channel, pocket, cavity), which can be disposed on sides (e.g., opposing sides) of a body portion of the button 770. The button 770 can be pushed further into the inner space 768 of the actuator 766 to position the one or more grooves 776 radially inward of the one or more locking features 772 of the actuator 766. The button 770 can be pushed into the inner space 768 until contacting an inner surface of the actuator 766 defining the inner space 768, which can align the one or more grooves 776 radially inward of the one or more locking features 772 of the actuator 766 and couple proximal advancement of the button 770 and actuator 766 together. With the one or more grooves 776 aligned radially inward of the one or more locking features 772, the button 770 and the actuator 766 can be pushed together, pushing the one or more locking features 772 of the actuator 766 against the one or more retention features 778 of the handle 762, which can urge (e.g., deflect) the one or more locking features 772 radially inward into the one or more grooves 776 of the button 770 to permit proximal advancement of the actuator 766 in the inner space 764 of the handle 762 to advance the push wire 738 and capture device 730 relative to the tube 744 such that the hook 734 is disposed outside of the tube 744 to release a stent 300 for delivery into the urethra.

The capture device 730, tube 744, and actuation mechanism 760 can be used with a delivery device, such as the cystoscope 700, to deliver the stent 300 into the prostatic urethra 106. The capture device 730 coupled to the actuation mechanism 760 by way of the push wire 738 can be inserted into the working channel 710 through the port 716 on the handpiece 704 at the distal end 708 of the cystoscope 700. The push wire 738 and body 736 of the capture device 730 can be disposed inside of the tube 744. The capture device 730 can be advanced into the catheter tube 702 by pushing the push wire 738 that is connected to the actuation mechanism 760. The tube 744 can be advanced with the capture device 730. The capture device 730 and tube 744 can be advanced through the working channel 710 until advancing out of the proximal end 718 of the cystoscope 700.

As shown in FIGS. 13A-13H, the actuation mechanism 760, the tube 744, and the capture device 730 can cooperate to securely capture and release the stent 300. In FIG. 13A, the actuator 766 is disposed inside the internal space 764 of the handle 762, with the one or more locking features 772 engaged with the one or more retention features 778. The button 770 is disposed inside the internal space 768 of the actuator 766 with the groove 776 just outside (e.g., distal) of the open mouth of the internal space 768. The state of the actuation mechanism 760, with the one or more locking features 778 engaged with the one or more retention features, as shown in FIG. 13A, corresponds to the state of the capture device 730 shown in FIG. 13B with the tubing 744 positioned against the distal-facing surface 733 of the tip 732 with the handle 324 of the stent 300 (not shown in FIG. 13B) securely held by the hook 734 of the capture device 730 disposed in the tube 744. The engagement of the one or more retention features 778 on the handle 762 and the one or more locking features 772 of the actuator 766 can exert tension on the push wire 738 and prevent accidental release of the stent handle 324. The engagement of the one or more retention features 778 of the handle 762 with the one or more locking features 772 of the actuator 766 can prevent advancement of the actuator 766 in the inner space 764 of the handle 762 such that the push wire 738 prevents relative advancement of the capture device 730 relative to the tube 744 to maintain the hook 734 coupled with the handle 324 of the stent 300 securely within the tube 744.

Figure 13C:
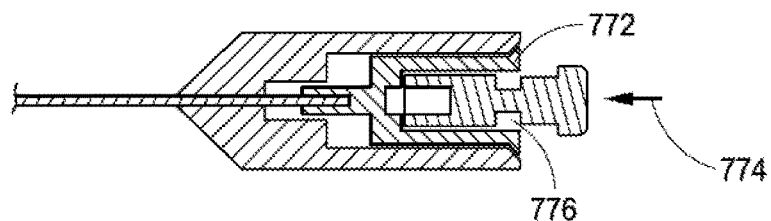
FIG. 13C illustrates the actuation mechanism after an initial force has advanced a button to position one or more recesses of the button radially inward of retention features of an actuator.

FIG. 13C shows a force 774 (e.g., pushing force) applied on the button 770. The force 774 can advance the button 770 in the inner space 768 of the actuator 766 until contacting a surface of the actuator 766 such as an inner surface of the inner space 764 of the actuator 766, which can couple proximal advancement of the button 770 and actuator 766 together. The one or more grooves 776 of the button 770, as a result of the force 774, can be positioned radially inward of (e.g., radially aligned with, proximate to) the locking features 772 of the actuator 766.

Figure 13D:
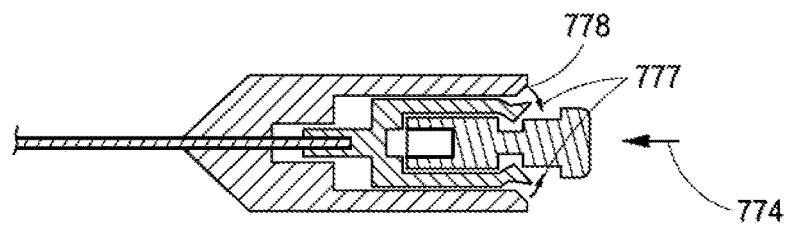
FIG. 13D illustrates the actuation mechanism after additional force has been applied to further advanced the button such that the retention features of the actuator deflect into the one or more recesses of the button.

As shown in FIG. 13D, the continued application of the force 774 on the button 770 transfers the force 774 to the actuator 766, which can push the one or more locking features 772 of the actuator 766 against the one or more retention features 778 of the handle 762. The one or more locking features 772 of the actuator 766 can deflect from contact with the one or more retention features 778 (e.g., angled surface) inward (e.g., radially inward) in the direction of arrows 777 into the one or more grooves of the button 770 such that the one or more locking features 772 and one or more retention features 778 are not engaged to prevent advancement of the actuator 766 in the inner space 764 of the handle 762.

Figure 13E:
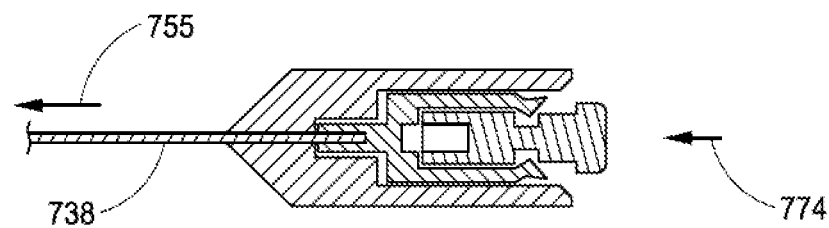
FIG. 13E illustrates the actuator, with the retention features deflected into the one or more recesses of the button, advanced relative to the handle to advance the push wire coupled to the capture device.
Figure 13F:
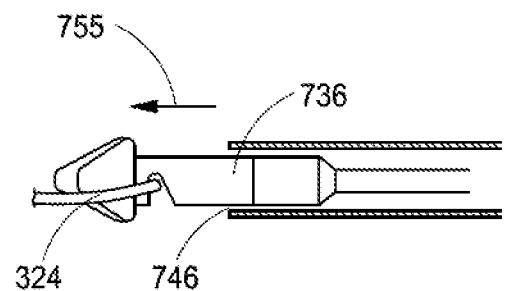
FIG. 13F illustrates the capture device advanced such that the hook of the capture device is disposed outside of the tube to deliver the stent to the urethra, which results from the advancement of the actuator illustrated in FIG. 13E.

As shown in FIG. 13E, the continued application of the force 774 on the button 770 can proximally translate the button 770 and actuator 766 in the inner space 764 of the handle 762. The actuator 766 can be pushed further into the internal space 764, causing a translational movement in a proximal direction 755 of the push wire 736 coupled to the actuator 766. Consequently, as illustrated in FIG. 13F, the translational movement causes the body 738 of the capture device 730 to be pushed out of the tubing opening 746 at the proximal end of the tube 744 so that the hook 734 is disposed outside of the tube 744. With the hook 734 disposed outside of the tube 744, the handle 324 of the stent 300 can be released from the hook 734, as shown in FIG. 13F, to deliver the stent 300 in the urethra.

Figure 13G:
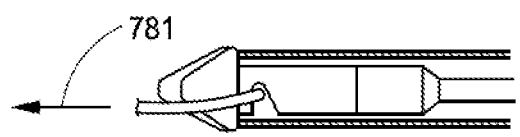
FIG. 13G illustrates the capture device with the hook coupled with the handle inside the tube securely retaining the handle when forces (e.g., axial forces) are applied to the stent.
Figure 13H:
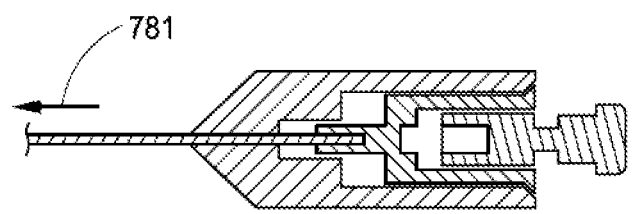
FIG. 13H illustrates the handle with the actuation mechanism coupled to the capture device in FIG. 13G retaining the position of the capture device despite a force being applied to the stent.

The actuation mechanism 760 can impede inadvertent release of the stent handle 324. For example, as shown in FIG. 13G, an axial force 781 (e.g., proximal axial force, pull force) can be applied to the stent 300 and/or the tip 732. The force 781 can be transferred from the capture device 730 through the push wire 738 to pull on the actuator 766. However, as illustrated in FIG. 13H, without the one or more grooves 776 of the button 770 aligned with the one or more locking features 772 of the actuator 766, the body of the button 770 can prevent inward deflection of the one or more locking features 772 such that the one or more locking features 772 remain engaged with the one or more retention features 778 of the handle 762 to prevent advancement of the actuator 766 within the inner space 764 and advancement of the capture device 730 relative to the tube 744 despite the axial force 781.

Figure 14A:
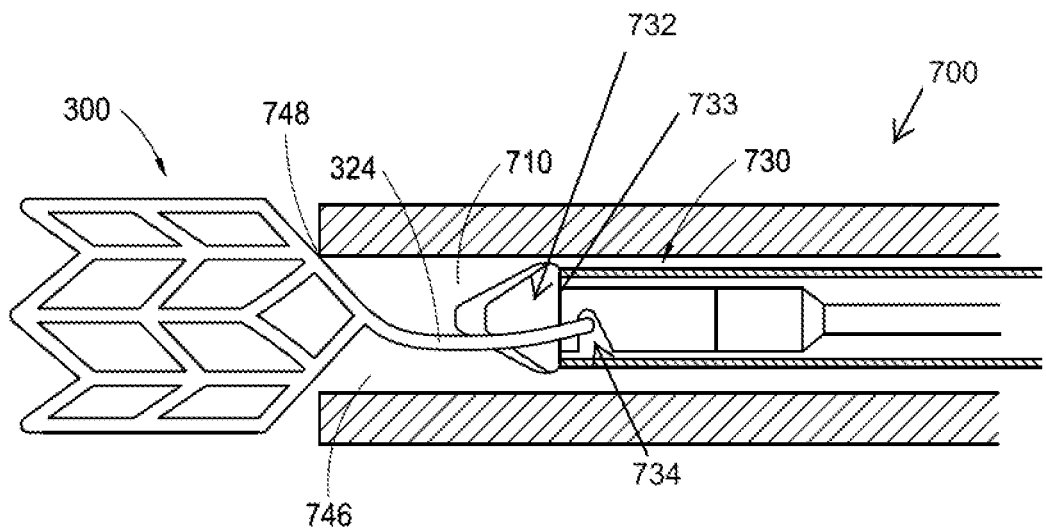
FIGS. 14A-14C illustrate schematic representations of a method of loading the stent into the work channel of the delivery device.
Figure 14B:
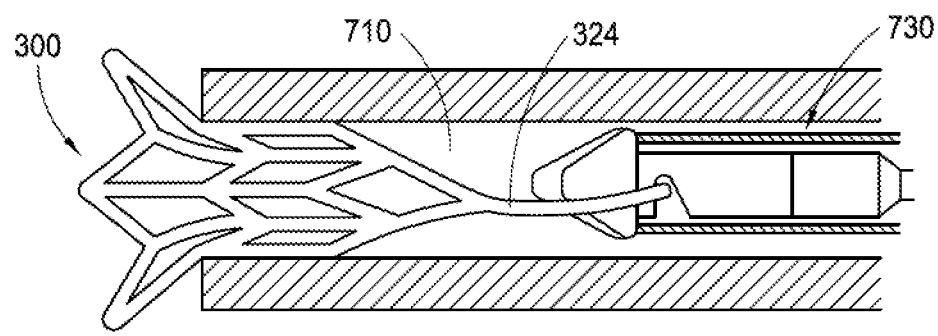
Figure 14C:
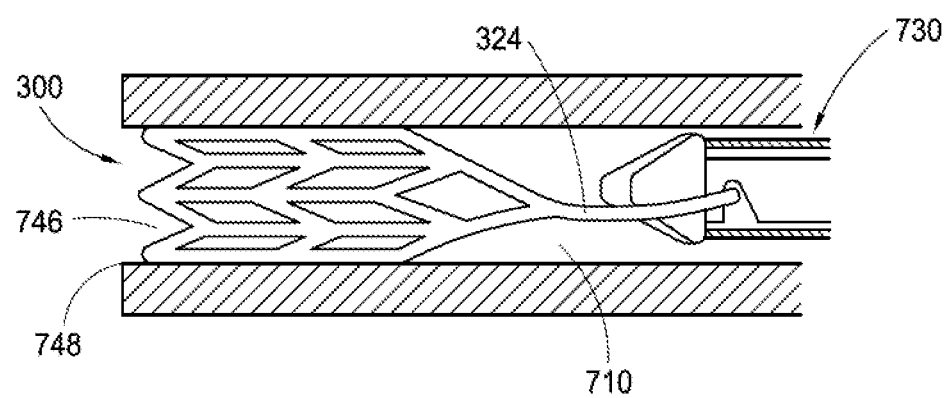

Referring to FIGS. 14A-14C, a method of loading a stent 300 in a work channel 710 of the cystoscope 700 is schematically illustrated. In FIG. 14A, the handle 324 of the stent 300 is securely captured by the hook 734 of the capture device 730 disposed in the tube 744 with the proximal end of the tubing 744 engaged with the distal-facing surface 733 of the tip 732. The handle 762 of the actuation mechanism 760 shown in FIGS. 13A-13H can be pulled by a clinician to retract the stent 300 into the work channel 710. As illustrated in FIG. 14A, the captured stent 300 can be initially retracted to contact an edge 748 of the opening 746 into the work channel 710 of the cystoscope 700. The handle 324 can be deflected to extend distally when pulled. As illustrated in FIG. 14B, with continued pulling of the handle 762, the stent 300 can be partially pulled into the work channel 710. The stent 300 can be collapsed by way of contact with the edge 748 as the stent 300 is pulled into the working channel 710 of the cystoscope 700. The stent 300 can be compressed to a size that fits the size (e.g., diameter) of the work channel 710. As illustrated in FIG. 14C, with continued pulling of the handle 762, the stent 300 can be fully loaded inside the working channel 710, which can include the stent 300 being collapsed in the working channel 710.

Figure 15A:
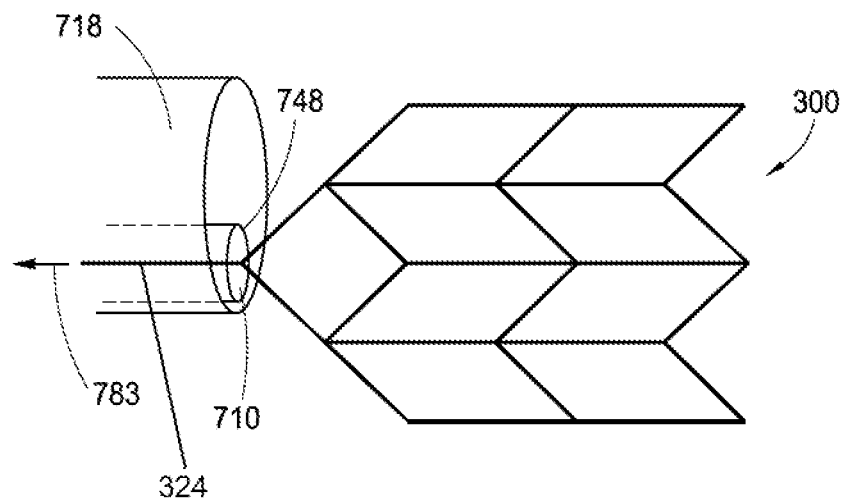
FIGS. 15A and 15B illustrate additional schematic representations of the stent loading method of FIGS. 14A-14C.
Figure 15B:
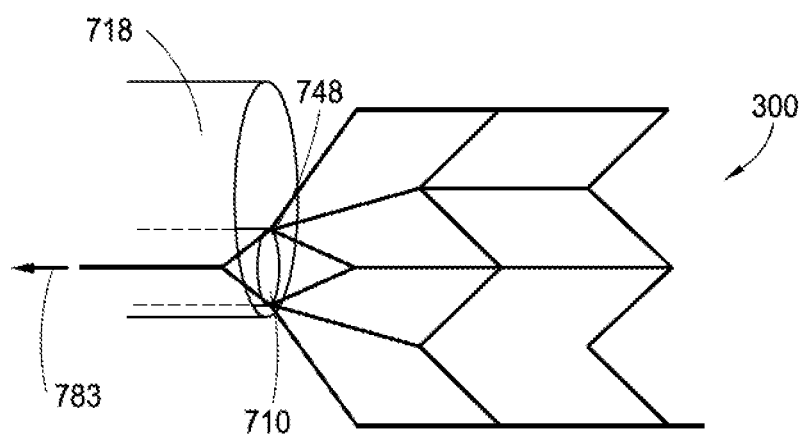

In some instances, the stent loading process and method described in reference to FIGS. 14A-14C can cause damage to the stent 300. When the handle 324 is pulled by the capture device 730 into the work channel 710, the stent 300 comes to be pressed against an edge 748 at the opening 746 at the mouth of the work channel 710. The edge 748, which may be approximately right angled, can contact points on the stent 300 (e.g., leading angled struts 312), which can concentrate forces on the stent 300. The individual forces on the contact points may not be uniformly distributed, so the forces at one point may be large enough to cause permanent deformations to the structure of the stent 300, including some longitudinal and angled struts 310 and 312. This can result in a deformed and/or crooked stent 300, which can negatively impact performance of the stent 300. This force concentration effect is illustrated in FIGS. 15A and 15B where a stent 300 is shown being pulled by a force 783 applied to the handle 324 into a work channel 710 through an opening on a proximal end 718. The work channel 710 can have an edge 748 (e.g., generally right-angle edge) at the open mouth into the work channel 710 that can compress the stent 300, as shown in the schematic view of FIG. 15B. As described, the edge 748 can concentrate forces on the stent 300, which can include unequal concentration, that damage the stent 300.

Figure 16A:
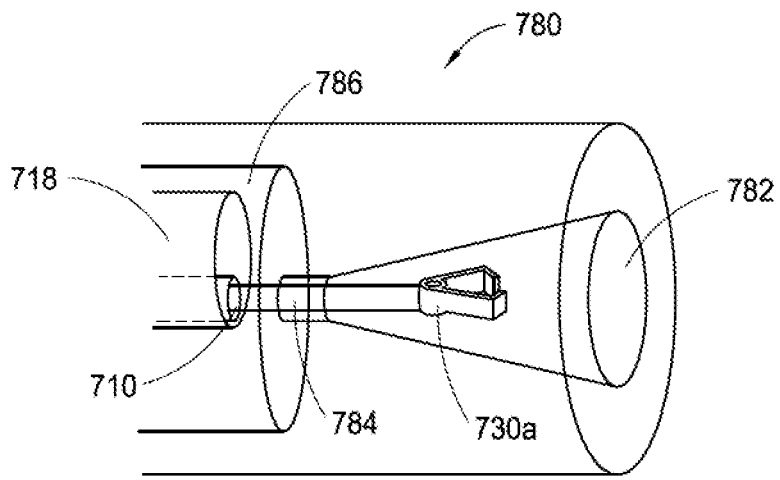
FIGS. 16A-16C illustrate schematic representations of a loading adapter disposed on a proximal end (e.g., end to be positioned in the urethra) of the delivery device to ease loading the stent into a working lumen of the delivery device.
Figure 16B:
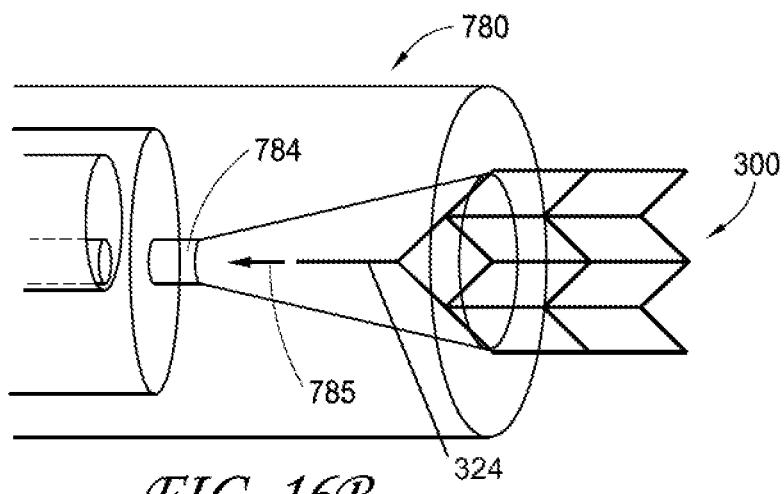
Figure 16C:
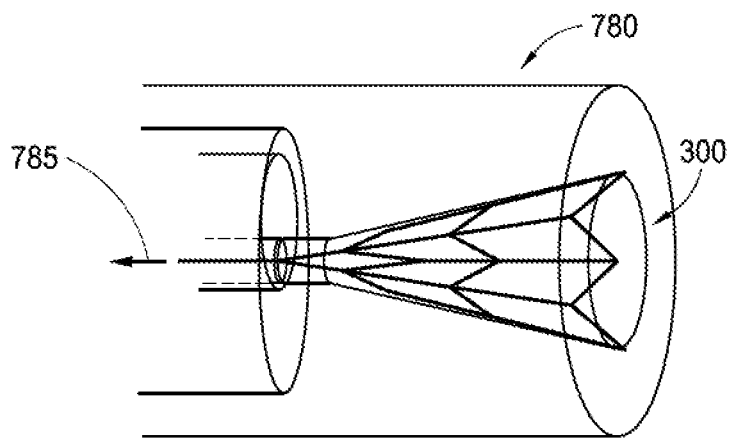

FIGS. 16A-16C illustrate a loading adapter 780 (e.g., loading tool, funnel adapter) that can ease loading the stent 300 into the working lumen 110 and/or more evenly distribute compressive forces on the stent 300 (e.g., reduce stress concentrators) to compress (e.g., collapse) the stent 300 for placement in the working lumen 110. The loading adapter 780 can include a port 782 (e.g., opening, funnel, mouth). The port 782 can include a cross-section that is tapered, which can include being gradually tapered in a proximal-distal direction. The side of the port 782 to be disposed next to the working channel 710 can include a size (e.g., diameter) and/or shape that is the same as (e.g., generally the same as) the working channel 710. The inner wall of the loading adapter 780 defining the port 782 can be tapered, which can define a receiving cross-section that gradually decreases in size (e.g., gradually decreases in size in the distal direction) to that of the working lumen 710. The distal portion of the port 782 can be smaller than the proximal portion of the port 782. The loading adapter 780 can include a lumen 784 (e.g., channel). The lumen 784 can include a consistent size and/or shape. The size and/or shape of the lumen 784 can be the same as the working channel 710, which can include the proximal opening into the working channel 710. The lumen 784 can be connected to the port 782 and match the work channel 710 on the proximal end 718 of the cystoscope by size. The lumen 784 and port 782 can be coaxially aligned. Because the proximal opening into the working channel 710 can be off a central longitudinal axis of the cystoscope 700, the port 782 and/or lumen 784 can be disposed off a central longitudinal axis of the loading adapter 780. To load a stent 300 into the work channel 710, the loading adapter 780 can be disposed on (e.g., capped on) the proximal end 718 of the cystoscope 700 shown in FIGS. 8A and 8B. The loading adapter 780 can be constructed to be disposed on other delivery devices or cystoscopes available on the market. Or different adapters 780 can be constructed for different cystoscopes. The loading adapter 780 can include a receiving space 786 (mating feature, key feature, receiving space, cavity, recess, channel) to mate with the proximal end 718 of the cystoscope. The receiving space 786 can be disposed on a side of the loading adapter 780 opposite the port 782. The receiving space 786 can be connected to the port 782, which can include being connected by way of the lumen 784. The receiving space 786 can receive a proximal end of the cystoscope to facilitate the loading adapter 780 being disposed on (e.g., capped on) the proximal end of the cystoscope. The loading adapter 780 can be disposed on the cystoscope and rotated to coaxially align the opening into the working channel 710 with the port 782. As shown in FIG. 16A, a capture device 730a, which can include a clamp (e.g., -clamp-like structure, grip, grasper) to grip the handle 324 of the stent 300, can be disposed through and out of the working channel 710. The capture device 730, described herein, can be disposed through and out of the working channel 710. The capture device 730a and/or capture device 730 can be used to coaxially align the working channel 710 and the port 782.

As shown in FIG. 16B, a stent 300 can be pulled by a pulling force 785 applied to the stent handle 324, which can be from the capture device 730a and/or capture device 730, into the loading adapter 780. The opening (e.g., distal opening) into the port 782 can be larger than the work channel 710, which can include being significantly larger. The diameter of the opening can be as big as or even larger than the diameter of the stent 300. In some embodiments, the diameter of the opening of the port 782 can be 10, 11, 12, 13, 14, 15, 16, 17, 18, 19, 20 mm, or even larger than 20 mm. The stent 300 can be pulled into the port 782, the nose end 318 (or distal end 308) of the stent 300 can start to be compressed first by the angled wall (e.g., tapered wall) of the loading adapter 780 defining the port 782. Then gradually the body section 320 of the stent 300 can be compressed, followed by the tail end 322 (or the proximal end 306). The pulling force 785 applied to the handle 324 that pulls the stent 300 into the port 782 can also pull the loading adapter 780 against the cystoscope (e.g., proximal face of the cystoscope). The taper (e.g., gradual taper) of the port 782 can distribute (e.g., uniformly distribute, evenly distribute) compresses forces on the stent 300 as the stent 300 is pulled into the port 782, which can avoid stress concentrates discussed herein that may be present without using the loading adapter 780. The taper of the port 782 can facilitate a gradual compression (e.g., collapse) of the stent 300 as the stent 300 is pulled further into the port 782, in contrast to an all-at-once approach without the loading adapter 780 as described herein. The taper of the port 782 can facilitate a smooth, consistent loading on the stent 300 to facilitate collapse. When the stent 300 reaches the distal portion of the port 782 (e.g., narrowed portion), the stent 300 can be compressed to a size that permits placement into the working channel 710. The loading adapter 780 can facilitate compressing force being more uniformly distributed compared to without using the loading adapter 780, as shown in FIGS. 14A-14C and FIGS. 15A and 15B. As shown in FIG.

16C, when the tail portion of the stent 300 enters the funnel port 782, the nose end may already be collapsed to about the size of the work channel 710. Further pulling at the stent 300 will cause the nose end 318 to smoothly enter the work channel 710, followed by the body 320 and the tail 322 smoothly and consistently. The use of the loading adapter 780 can avoid damage to the stent 300 when being loaded into the working channel 710. As such, crooked or deformed stents 300 can be avoided.

Figure 17A:
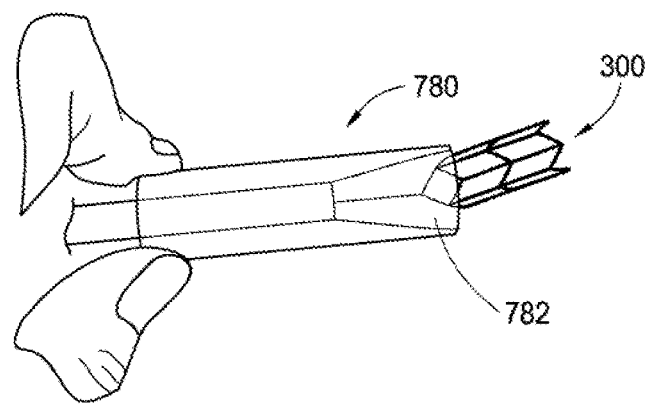
FIGS. 17A-17C illustrate additional schematic representations of the loading adapter being used to load the delivery device into the working lumen of the delivery device.
Figure 17B:
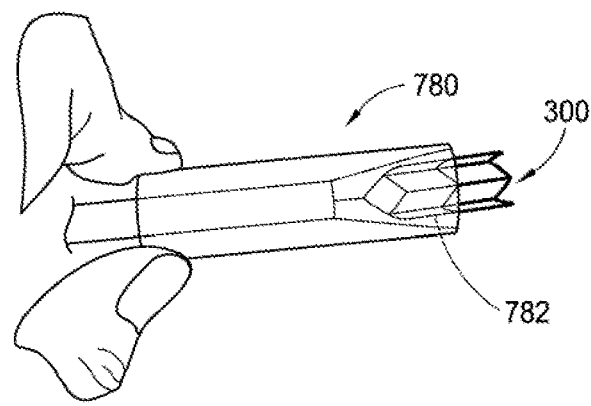
Figure 17C:
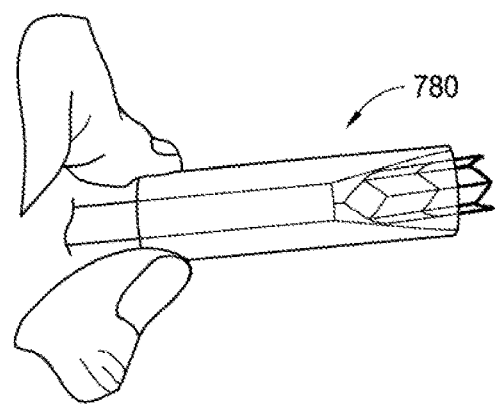

As shown in FIGS. 17A-17C, the loading adapter 780 can automatically align the stent 300 to be coaxially positioned relative to the port 782 and/or working channel 710 as the stent 300 is pulled into the port 782. As the stent 300 is pulled into the port 782 by the capture device 730 or 730a, the central longitudinal axis of the stent 300 may not be coaxially aligned with the central longitudinal axis of the port 782, as shown in FIG. 17A. However, the taper cross-section (e.g., wall) of the port 782 can center the stent 300 relative to the port 782 as the stent 300 is pulled into the port 782, which can include coaxially aligning the stent 300, port 782, and/or working channel 710 as illustrated in FIGS. 17B and 17C. The tapered wall of the port 782 can push on edges or struts of the stent 300 that contact the port 782 first to coaxially align the stent 300, port 782, and/or working channel 710. As such, misalignment can be corrected.

Figure 18A:
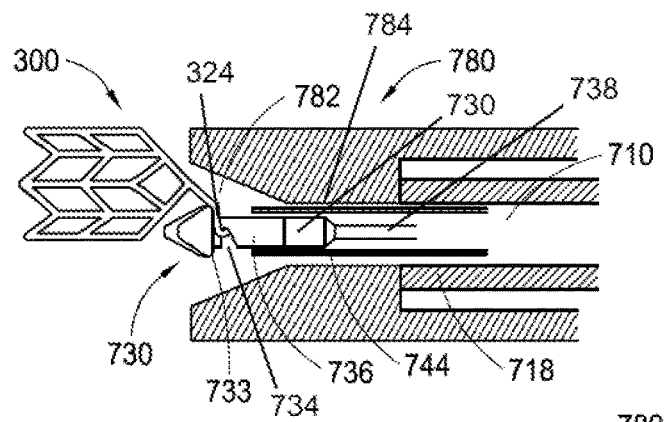
FIGS. 18A-18E illustrate schematic representations of a method of loading the stent into the work channel of the delivery device using the loading adapter.

In FIGS. 18A-18E, a stent loading process is shown with the capture device 730, tube 744, funnel adapter 780, handle 762 with the actuation mechanism 760, and working channel 710 of the delivery device (e.g., cystoscope 700). The loading adapter 780 can be disposed on a proximal end of the delivery device (e.g., cystoscope 700). The loading adapter 780 can be maneuvered (e.g., rotated) to coaxially align the port 782 and proximal opening of the working lumen 710. In FIG. 18A, the capture device 730 is pushed out of the work channel 710 and through the port 782 of the loading adapter 780, which is mated on to the proximal end 718 of cystoscope 700. In some embodiments, the capture device 730 can be advanced out of the working channel 710, prior to placing the loading adapter 780, to help coaxially align the port 782 and the working channel 710 as described herein. The capture device 730 (e.g., body 736) can be advanced relative to the tube 744 such that the hook 734 is exposed outside of the tube 744 to capture the handle 324 of the stent 300. The capture device 730 can be advanced relative to the tube 744 using the techniques described herein (e.g., FIGS. 13A-13H). The clinician can position the stent handle 324 in the hook 734 of the capture device 730.

Figure 18B:
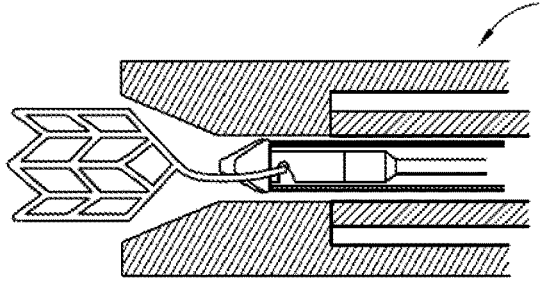

As shown in FIG. 18B, the capture device 730 and the tube 744 can be moved relative to each other to position the distal-facing surface 733 in contact with the proximal end of the tube 744 and/or position the hook 734 in the tube 744, as described in reference to FIGS. 11A and 11C, to securely couple the capture device 730 with the handle 324 of the stent 300. In some embodiments, the button 770 of the actuation mechanism 760 can be pulled to translate the actuator 766 (which is coupled to the capture device 730 by way of the push wire 738) from the configuration illustrated in FIG. 13E to that illustrated in FIG. 13C with the one or more locking features 772 of the actuator 766 engaged with the one or more retention features 778 of the handle 762 (see FIGS. 13A-13D). The one or more locking features 772 of the actuator 766 deflected into the one or more grooves 776 of the button 770 can couple translational movement of the actuator 766 and button 770 together to facilitate movement from the configuration illustrated in FIG. 13E to that in FIG. 13C by pulling on the button 770. The distal movement of the actuator 766 can, by way of the push wire 738 coupled to the capture device 730, cause corresponding distal movement of the capture device 730. In some embodiments, the tube 744 may be advanced relative to the capture device to place in the configuration illustrated. With the stent handle 324 captured by the capture device 730 and tube 744, the capture device 730 and tube 744 can be retracted distally to pull the stent 300 through the port 782 of the loading adapter 780 and into the working channel 710 of the delivery device (e.g., cystoscope 700). The handle 762 can be pulled distally to pull the stent 300 through the port 782 of the loading adapter 780 and into the working channel 710 of the delivery device (e.g., cystoscope 700). The nose end of the stent 300 is initially come in contact the port 782. The tapered port 782 of the loading adapter 780 can ease loading of the stent 300 as described herein.

Figure 18C:
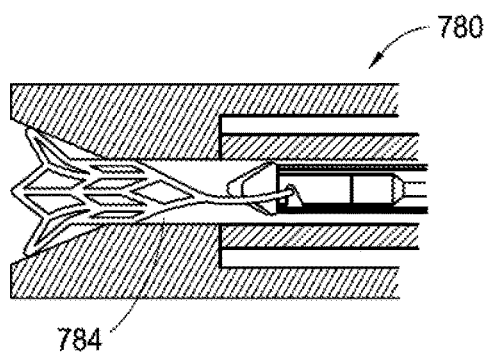
Figure 18D:
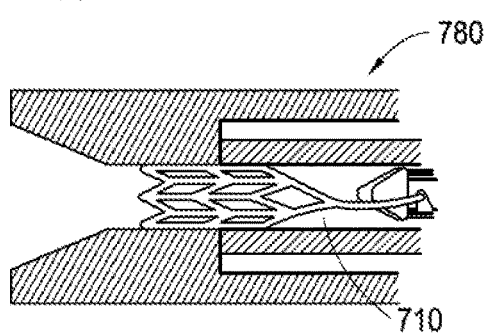
Figure 18E:
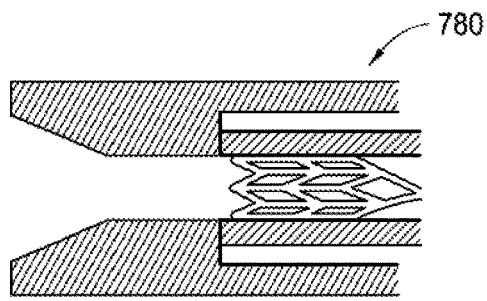

In FIG. 18C, the stent 300 is further pulled into the port 782, causing a part of the stent 300 at the nose end to collapse and be pulled into the lumen 784 of the loading adapter 780. The tail end is also partially collapsed due to compression from the tapered port 782 of the loading adapter 780. In FIG. 18D, with continued pulling, the stent 300 can be collapsed to a size to be received in the working channel 710. The stent 300, as illustrated in FIG. 18D, can be partially in the lumen 784 and partially in the work channel 710. In FIG. 18E, the stent 300 is fully pulled into the work channel 710. At the point, the tail 322 of the stent 300 may be slightly inside the work channel 710 or flush with the face of the work channel 710. When loading the stent 300 into the working channel 710 of a delivery device, such as the cystoscope 700, the handle 324 may be tucked downward and folded such that the folded handled 324 is pulled into the working channel. The handle 324 can be deflected to a position, as illustrated in FIGS. 18B-18D, with the handle 324 aligned with the central longitudinal axis of the stent 300, as described herein. The overall length of the collapsed stent with folded handle may be about 38 mm, and the diameter may be about 2.2 mm. In some embodiments, the overall length of the collapsed stent with folded handle is between about 22 and 52 mm, or about 22, 25, 28, 31, 34, 37, 40, 43, 46, 49, or 52 mm.

Figure 19A:
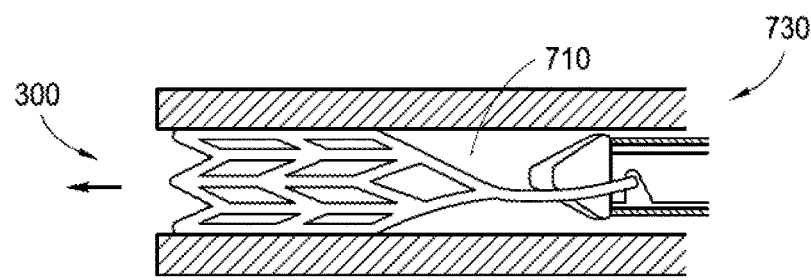
FIGS. 19A-19E illustrate schematic representations of a method of delivering the stent into a prostatic urethra.
Figure 19B:
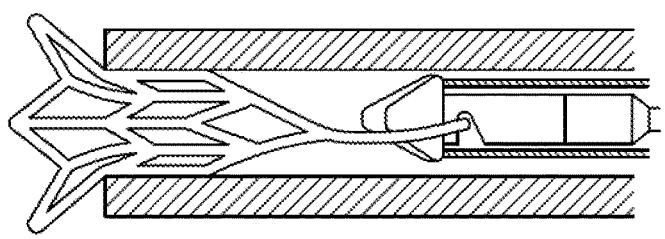
Figure 19C:
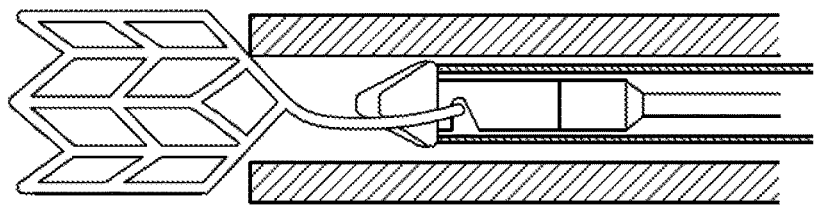
Figure 19D:
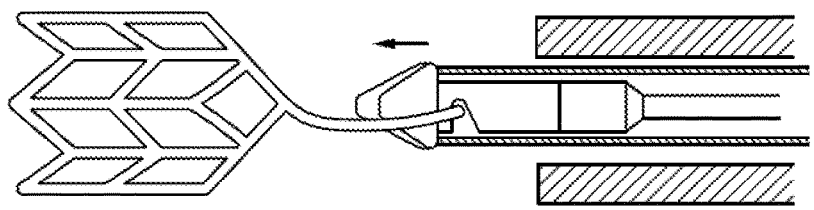
Figure 19E:
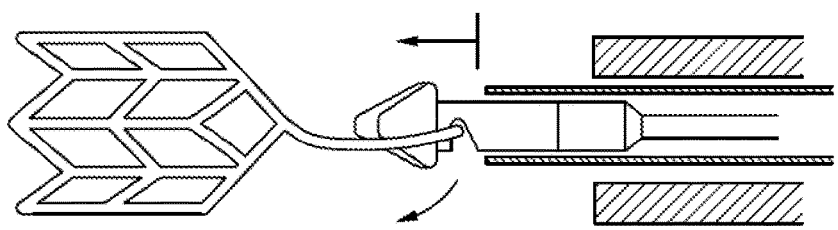

When the stent 300 is loaded, the loading adapter 780 can be removed from the proximal end 718 of the cystoscope 700. FIGS. 19A-19E illustrate a process for delivering a loaded stent into a prostatic urethra of a patient. In FIG. 19A, a force is pushed on the capture device 730 and transferred to the stent 300 to move the stent 300 proximally toward the proximal opening of the working lumen 710. For example, the handle 762 can be advanced by a clinician, relative to the delivery device (e.g., cystoscope 700), which can cause the push wire 738 to advance the capture device 730 and tube 744. The advancement of the capture device 730 and tube 744 with the stent handle 324 captured can advance the stent 300 proximally in the working lumen 710. In FIG. 19B, the tail end 322 of the stent 300 is pushed out of the work channel 710 and immediately starts to expand its shape, which can contact the urethra for positioning. In FIG. 19C, the body 320 of the stent 300 is pushed out of the work channel 710, and the stent 300 is expanded. In FIG. 19D, the entire stent 300, including the handle 324, is pushed out of the work channel 710. With the handle 324 still captured by the hook 734, the clinician can adjust the axial and radial positions of the stent 300 in the urethra. Visualization, e.g., fluoroscopy, may guide the delivery procedure. In FIG. 19E, the hook body 736 is partially pushed out of the tubing 744 to expose the hook 734 as described in reference to FIGS. 13A-13F. As such, the stent handle 324 is released to spring back toward its original shape, under the constraints inside the urethra. The handle 324, as described herein, can engage the wall of the urethra to hold the stent 300 in place. This process is actuated with the actuation mechanism 760 at the distal end 708 of the cystoscope 700.

Figure 20A:
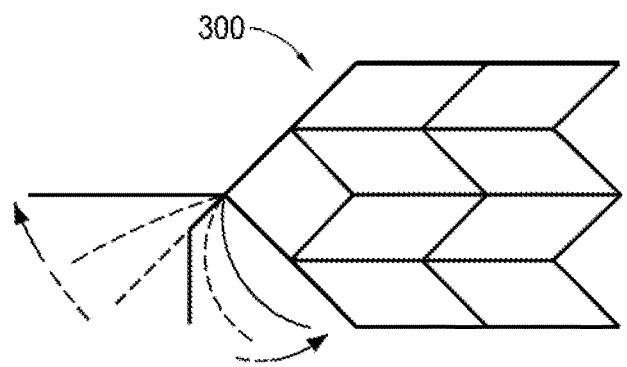
FIG. 20A illustrates deflection of the stent handle.
Figure 20B:
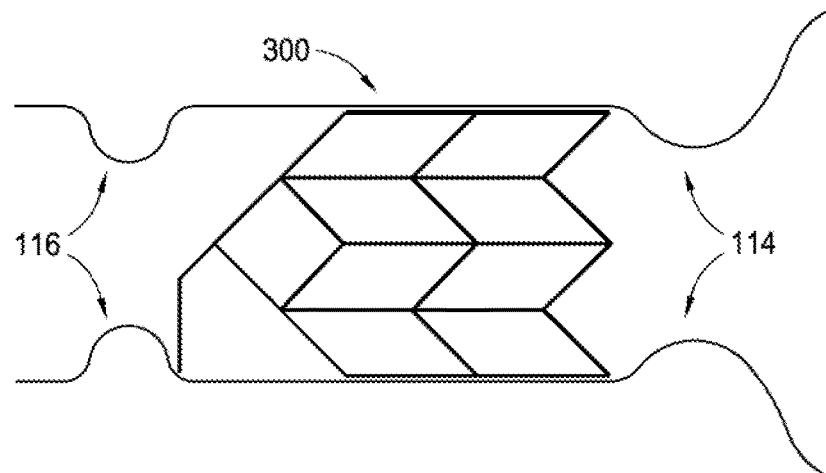
FIGS. 20B and 20C illustrate schematic representations of the urethral stent disposed within the prostatic urethra between the bladder neck and apex at the verumontanum.
Figure 20C:
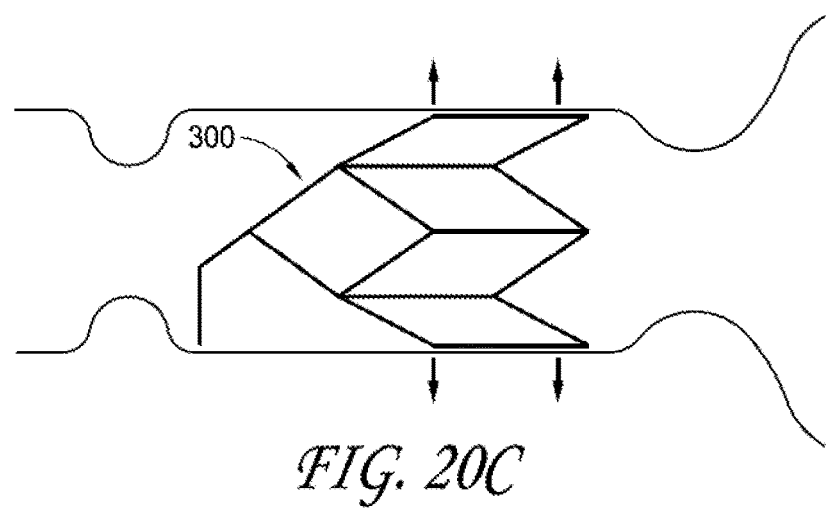

The handle 324 of the stent 300 may also facilitate the retrieval of a deployed stent by providing a connection point to a control mechanism, such as the capture device 730 or 730a. Once the control mechanism is inserted into the prostatic urethra and connects to the stent handle, the stent may be drawn into the working channel of a deployment device by pulling the control device through the working channel and drawing the stent into the working channel, as at least shown in FIGS. 11A-11C and 14A-14C. During retrieval, the handle may swing outward such that it is aligned with the longitudinal axis of the stent, as shown in FIG. 20A. Once implanted in the prostatic urethra, the handle automatically moves to a folded position, pointing downward. The handle, with the divot at its center, can be used to anchor the stent in the prostatic urethra. For example, the divot may be positioned to contact, embed, and/or abut the distal end 116 (e.g., apex at the verumontanum) of the prostatic urethra 106. In some embodiments, the stent 300 is positioned such that the divot and/or handle contact, embed, and/or abut the verumontanum which is more proximal to the distal end 116. The divot and/or handle can be disposed proximal (e.g., tucks behind, contacts, embeds proximally) of the apex 116 at the verumontanum. The proximal end of the stent 300 (e.g., the leaflets or tail tips) can embed against or abut the proximal end 114 of the prostatic urethra 106 or the bladder neck wall to prevent proximal migration of the stent. The overall stent length is chosen to match the overall length of the prostatic urethra.

A clinician may measure the length of the prostatic urethra and then select a stent having a length that is about equal to or slightly less than the prostatic urethra length. In some embodiments, the overall length of the stent is 15, 20 or 25 mm. The length of the stent is selected to match the prostatic urethra length to assure that the handle may function as an anchor and abut against the apical margin of the prostatic urethra while the distal leaflets abut the bladder neck.

Figure 21:
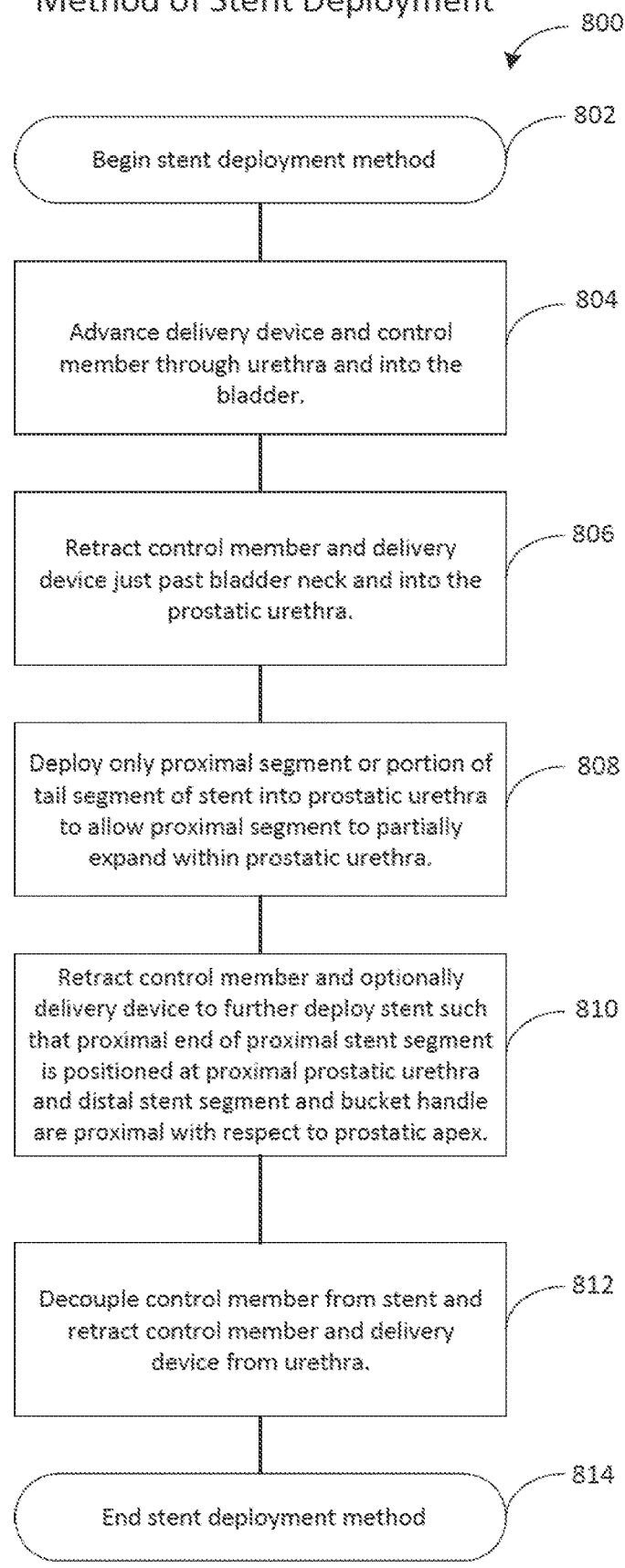
FIG. 21 is a flow chart illustrating a method of deploying a urethral stent.

FIG. 21 is a flow chart illustrating one embodiment of a method 800 of deploying a urethral stent, such as any of the stents described herein, in the prostatic urethra. A delivery device, such as the delivery device of FIGS. 8A and 8B (e.g., the cystoscope 700) or any other delivery device, is provided. A urethral stent, such as any of the stents described herein, is loaded into and positioned near the distal end of the delivery device's catheter body. The stent is releasably attached to an elongate control member, such as the capture device 730 or 730a as described herein, that extends through the delivery device's working channel and secures to the stent at the control member's distal end and the stent's handle.

Figure 22A:
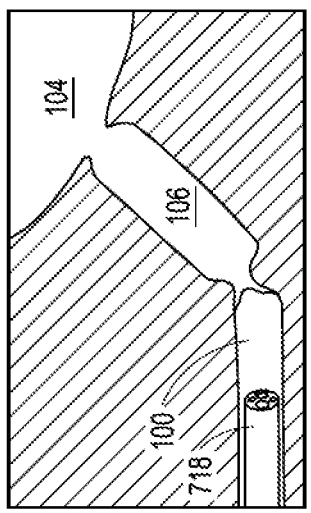
FIGS. 22A-22L illustrate the deployment of a urethral stent according to the method of FIG. 21.
Figure 22B:
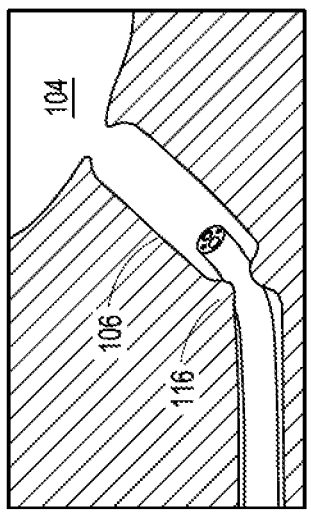
Figure 22C:
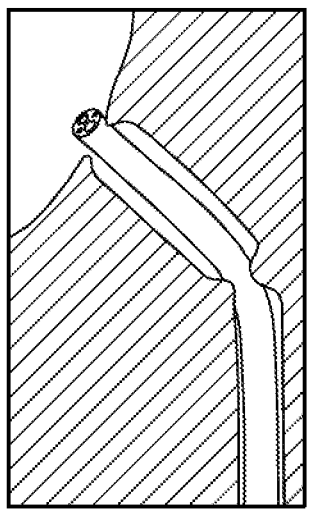
Figure 22D:
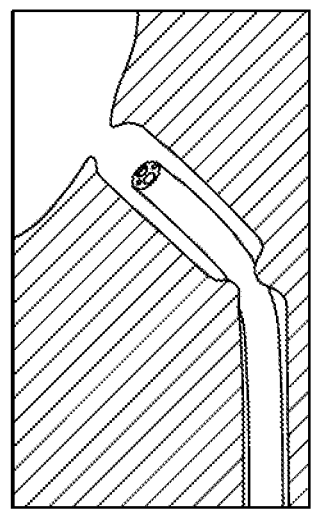
Figure 22E:
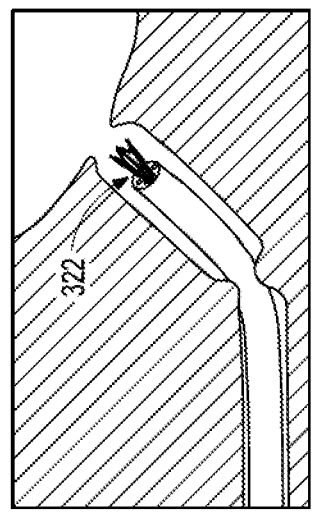
Figure 22F:
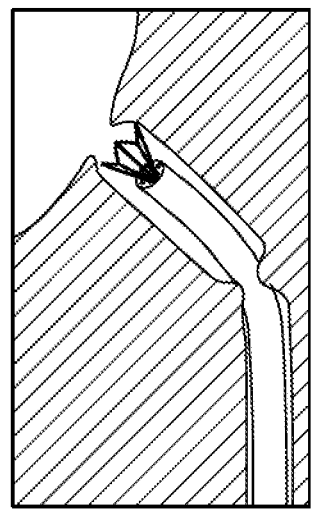
Figure 22G:
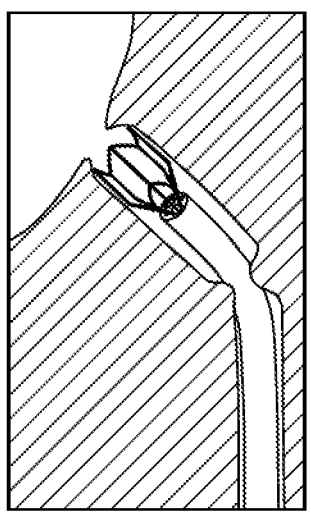
Figure 22J:
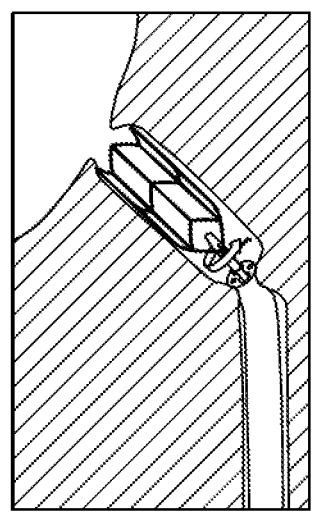
Figure 22H:
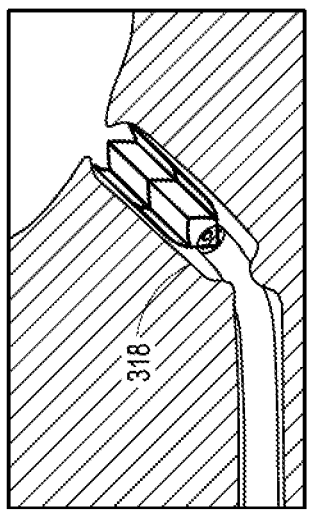
Figure 22K:
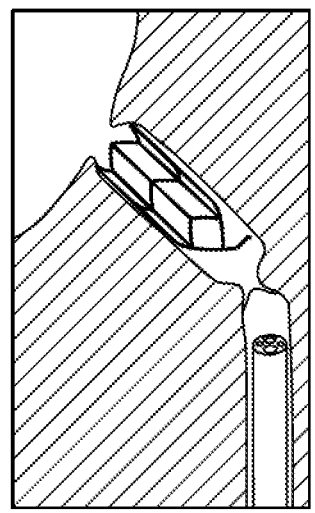
Figure 22I:
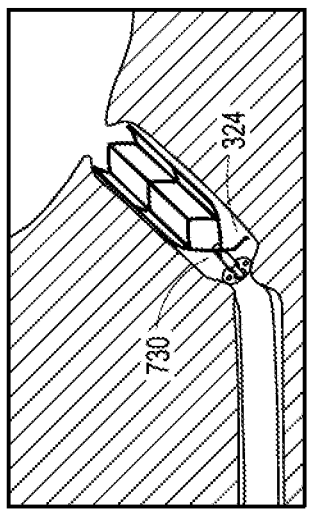
Figure 22L:
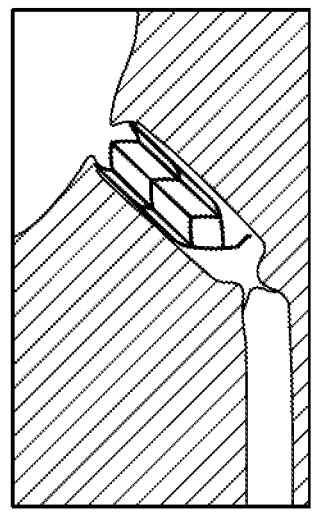

The method 800 begins at block 802. At block 804, the delivery device and control member are advanced through the urethra in a proximal direction towards the bladder 104 (see FIGS. 22A and B). The delivery device and control member are advanced until the proximal end 718 of the delivery device and control member are slightly within the bladder 104 (see FIG. 22C). At block 806, the delivery device and control member are withdrawn in a distal direction to position the proximal end 718 of the delivery device within the prostatic urethra 106, just next to the bladder neck (see FIG. 22D). At block 808, the proximal segment or a portion of the tail segment of the stent 300 is deployed by advancing the control member with respect to the delivery device while retracting the delivery device distally, which results in partially pushing the stent 300 out of the delivery device's working channel 710 and into the prostatic urethra 106 (see FIG. 22E). The deployed portion of the tail segment of the stent 300 expands within the bladder and may be pressed into the bladder neck (see FIG. 22F). At block 810, the delivery device is further retracted while holding the control member at a fixed position, or while pushing the control member proximally, until the proximal end of the proximal segment is positioned at the proximal prostatic urethra (see FIG. 22G). The remaining length of the stent 300 may then be deployed in a similar manner, by pulling the delivery device while holding or pushing the control member (see FIGS. 22H-22I). At block 812, the control member may then be decoupled from the stent handle 324 (see FIG. 22J), and the control member and the delivery device may then be retracted distally (see FIG. 22K) and withdrawn from the urethra, leaving the stent 300 positioned within the prostatic urethra 106 (see FIG. 22L). The control member may be decoupled from the stent 300 (e.g., stent handle 324) by rotating the control member, releasing a grasping member (e.g., clamp of the control member 730a), unhooking one from the other, and/or using any other coupling and decoupling method described herein. The method 800 ends at block 814.

Figure 23:
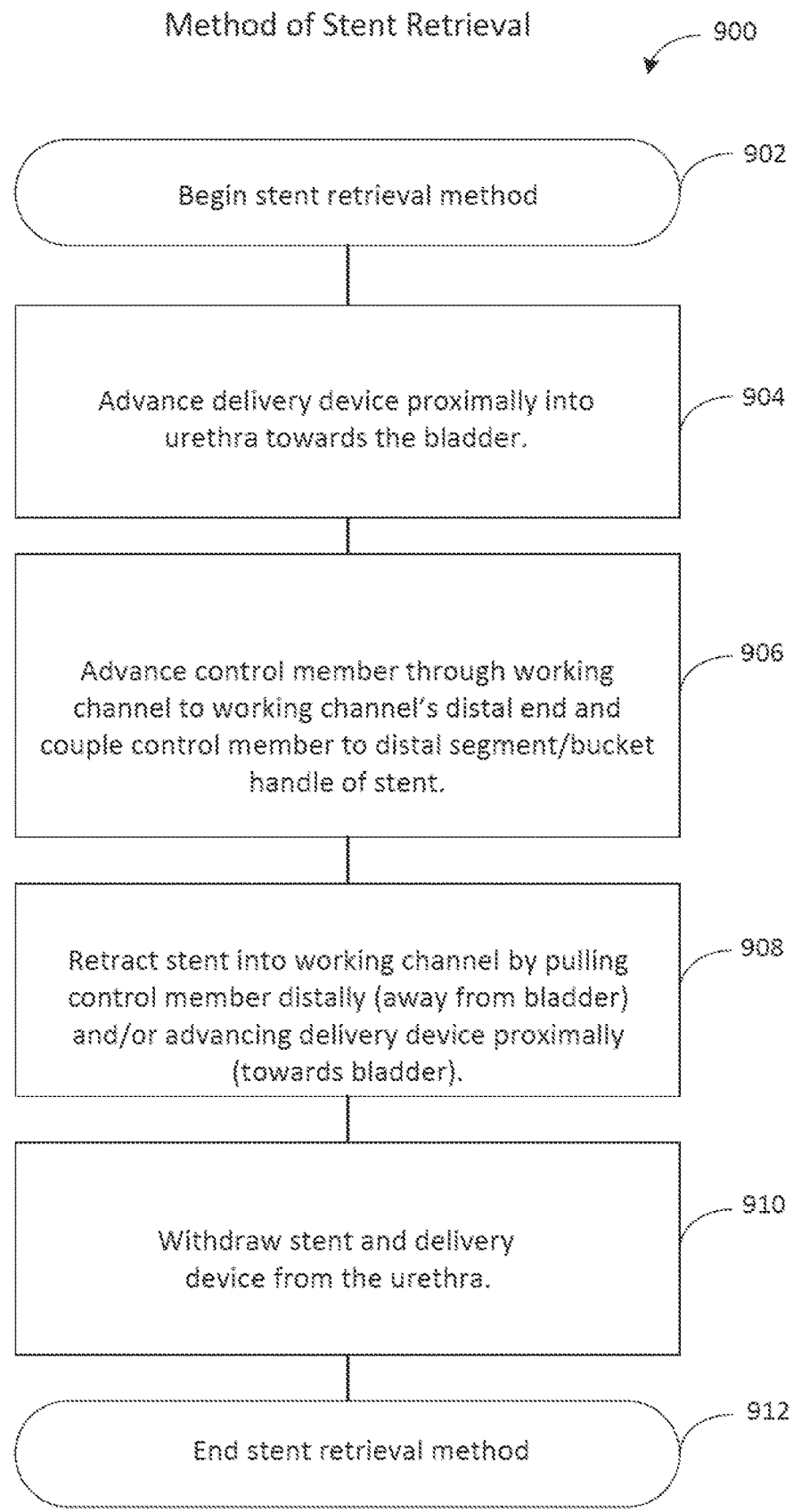
FIG. 23 is a flow chart illustrating a method of retrieving a urethral stent.

FIG. 23 is a flow chart illustrating one embodiment of a method 900 of retrieving a urethral stent, such as any of the stents 300 described herein, in the prostatic urethra 106. A delivery device, such as the delivery device of FIGS. 8A and 8B or any other delivery device, is provided. A urethral stent, such as any of the stents 300 described herein, is located within a patient's prostatic urethra. A control member (e.g., capture device 730 or 730a) configured to releasably couple to the stent is provided within the working channel of the delivery device.

The method 900 begins at block 902. At block 904, the delivery device is advanced through the urethra in a proximal direction towards the bladder. The delivery device is advanced until the distal end of the catheter is adjacent or near the distal end/nose segment or handle of the stent. At block 906, a control member is advanced though the delivery device's working channel to the working channel's proximal end. The control member is attached to the stent nose segment at the stent's handle, which can be performed using any of the techniques described herein in reference to the capture device 730 or 730 coupling with the stent handle 324 of the stent 300. At block 908, the control member is then withdrawn in a distal direction (towards the delivery device's distal end), thereby pulling the control member and the stent into the delivery device's working channel. Alternatively, or in addition, the delivery device may be advanced proximally (towards the bladder) to capture the stent within the delivery device's working channel. Contact between the working channel inside perimeter and the stent causes the stent to collapse radially as it is moves distally and into the working channel. Once the stent has been captured partially or completely within the working channel, at block 910 the stent and delivery device may be withdrawn and removed from the urethra. The method 900 ends at block 912.

Figure 24:
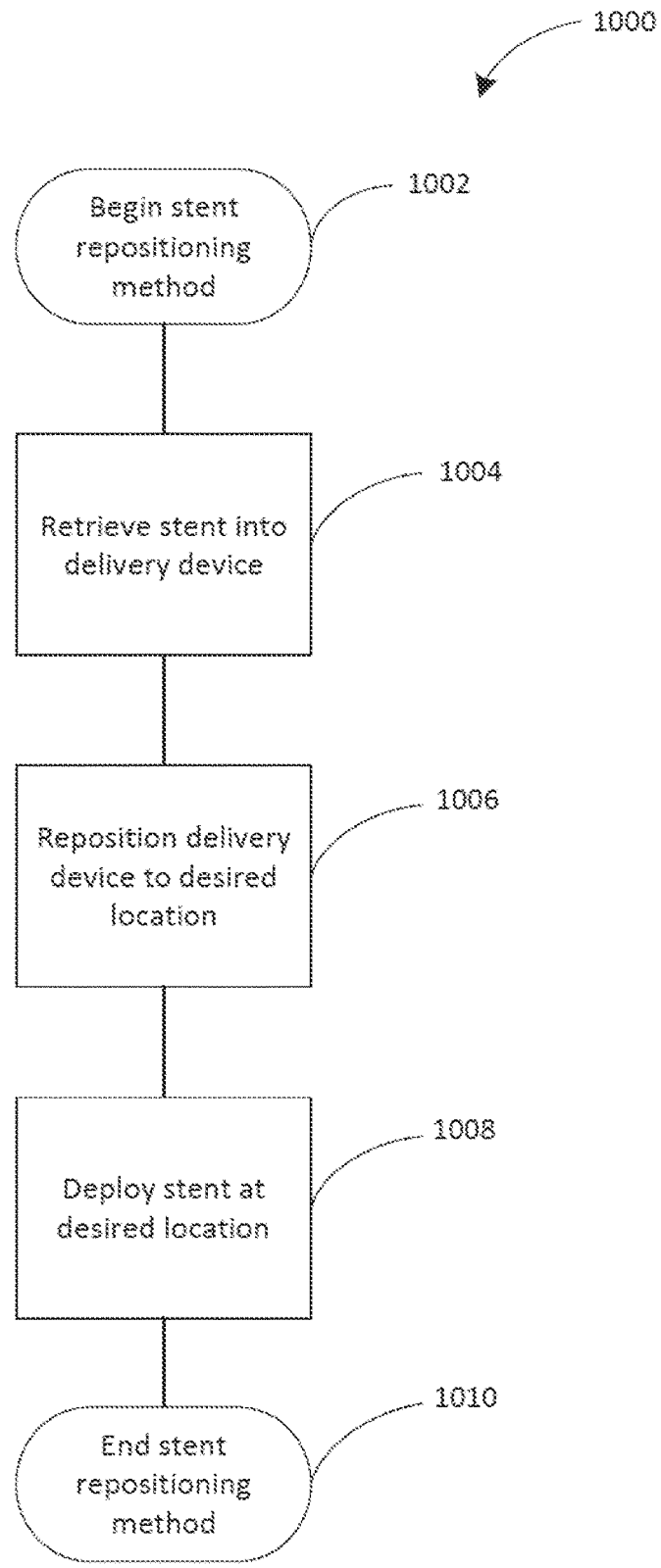
FIG. 24 is a flow chart illustrating a method of repositioning a urethral stent.

FIG. 24 is a flow chart illustrating one embodiment of a method 1000 of repositioning a urethral stent, such as any of the stents 300 described herein, in the prostatic urethra 106. A delivery device, such as the delivery device of FIG. 8A or 8B or any other delivery device, is provided. A urethral stent, such as any of the stents described herein, is located within a patient's prostatic urethra.

The method 1000 begins at block 1002. At block 1004, the stent is initially retrieved into the working channel of a delivery device, for example, according to the method described above with respect to FIGS. 13A-13H. The stent can be retrieved into the working channel with the capture device 730 or 730a. At block 1006, the delivery device and captured stent are then repositioned to a new desired location. For example, the delivery device and stent may be positioned at the proximal prostatic urethra, or at any other desired location. At block 1008, the stent is then deployed, for example, according to the method described above with respect to FIG. 21. At block 1010, the method 1000 can end.

Figure 25:
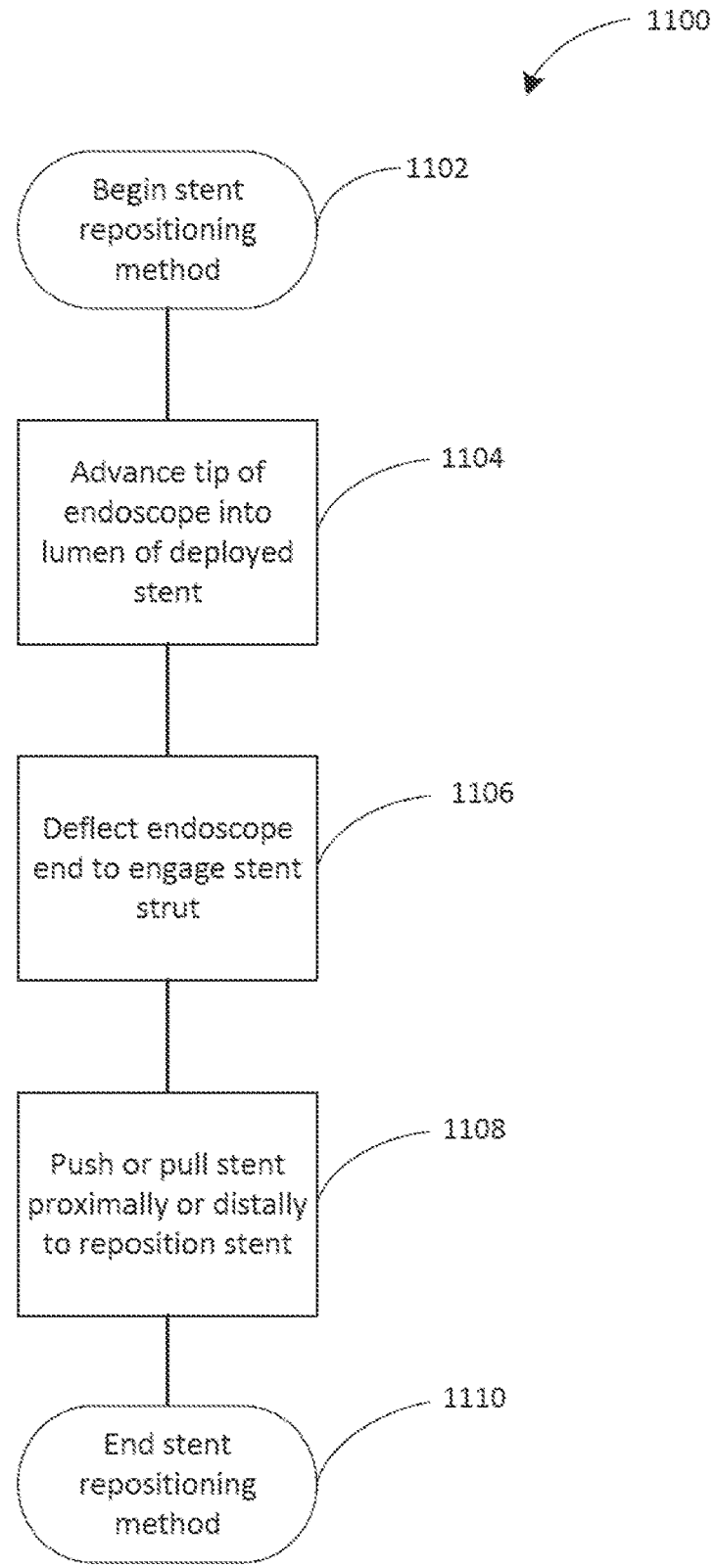
FIG. 25 is a flow chart illustrating a method of repositioning a urethral stent.

FIG. 25 is a flow chart illustrating another embodiment of a method 1100 of repositioning a stent without retracting the stent into the working channel of an endoscope. The method 1100 begins at block 1102. At block 1104, the tip of an endoscope is advanced into the lumen of the stent. At block 1106, the endoscope end is deflected to engage a stent strut. For example, a control at the distal end of the endoscope may be used to deflect the proximal end of the endoscope (e.g., upward or downward). Such controls are used to steer the endoscope through the patient's vasculature. However, in this embodiment, endoscope deflection is used to deflect the proximal end of the endoscope to cause it to lock onto, or to engage a strut of the stent. Once engaged, at block 1108, the operator may apply linear force to the endoscope to push or pull the stent in the proximal or distal direction. The operator can visualize stent movement vis-à-vis the mucosa of the urethral lumen, allowing for estimation of linear movement. Once the stent is positioned at the desired location, the method 1100 ends at block 1110. This technique allows repositioning of the stent without needing to pull the stent back into the working channel of an endoscope.

The stents described herein may be further described by their length, expanded diameter, collapsed diameter, angle values, and strut/wall thickness. A variety of values and combinations of values are possible and should not be limited to the following examples. In some embodiments, the stent has an outside, expanded diameter in the range of about 8 mm to about 12 mm. The overall length of the stent may be in the range of about 15 mm to about 45 mm. The nose segment of the stent may have a length of about 10 mm and the body may have a length of about 15 mm and the length of the tail may be selected such that the overall stent length matches the patient's anatomy. For example, the tail segment may have a length of about 5 mm to about 30 mm. The acute angles within the stent cells may be in the range of 5 to 85 degrees, 10 to 60 degrees or 20 to 50 degrees. The obtuse angles within the stent may be in the range of 95 to 175 degrees, 120 to 170 degrees, or 110 to 150 degrees. The strut and wall thickness of the stent can be in the range of 0.025 mm and 1.0 mm.

Other Considerations

It is contemplated that various combinations or sub-combinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting the device proximate to the distal end of the prostatic urethra" includes "instructing the inserting a device proximate to the distal end of the prostatic urethra." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A device configured to maintain patency of a prostatic urethra, the device comprising:
    a stent comprising:
        a proximal end;
        a distal end;
        a passageway between the proximal and distal ends, the passageway configured to facilitate a flow of a bodily fluid from the proximal end to the distal end when the stent is implanted in a prostatic urethra of a patient;
        a peripheral wall disposed about the passageway, the peripheral wall comprising a plurality of struts and a plurality of nodes coupled to each other to form a plurality of cells; and
        a handle formed from a most distal strut of the plurality of struts, wherein the handle is biased to a first position such that the handle is substantially coplanar with the peripheral wall when viewed from an axial direction, and such that the handle does not impede flow of the bodily fluid through the passageway when the stent is implanted in the prostatic urethra of the patient, wherein the handle is configured to extend in a distal direction beyond a most distal cell of the plurality of cells of the peripheral wall when the stent is expanded, wherein while biased to the first position, a portion of the handle extends in a direction perpendicular to a longitudinal axis of the stent, and wherein the handle is further configured to engage a wall of the prostatic urethra;
        wherein the stent is configured to expand from a compressed configuration to an expanded configuration within the prostatic urethra; and
        wherein the handle is configured to be deflected from the first position to a second position, when the handle is pulled in the distal direction, wherein the second position is closer to a central longitudinal axis of the stent compared to the first position.

2. The device of claim 1, wherein, in the second position, the handle extends in a direction that is substantially the same as the central longitudinal axis of the stent.

3. The device of claim 1, wherein, in the second position, the central longitudinal axis extends through the handle.

4. The device of claim 1, wherein the handle is disposed on the distal end of the stent with the stent disposed in the prostatic urethra.

5. The device of claim 1, wherein the handle comprises a curve biasing the handle to the first position.

6. The device of claim 1, wherein, in the first position, the handle extends from distal struts of the plurality of struts and curves to extend in a direction substantially perpendicular to the central longitudinal axis of the stent.

7. The device of claim 1, wherein the handle comprises a divot configured to engage with a capture device for loading the stent into a working lumen of a delivery device, and wherein portions of the strut on opposite sides of the divot are substantially colinear and orthogonal to both the longitudinal axis of the stent and the portion of the handle extending in the direction perpendicular to the longitudinal axis of the stent.

8. The device of claim 7, wherein the divot is configured to protrude distally with the stent disposed in the prostatic urethra.

9. The device of claim 1, wherein the stent comprises a collapsibility gradient between the proximal and distal ends.

10. The device of claim 1, wherein the plurality of struts and the plurality of nodes form circumferential rings.

11. The device of claim 10, wherein the circumferential rings provide different outward radial forces.

12. The device of claim 10, wherein the circumferential rings include struts of the plurality of struts in a Z pattern.

13. The device of claim 10, wherein the circumferential rings include angled struts of the plurality of struts in an alternating pattern of distal-angled struts and proximal-angled struts.

14. The device of claim 1, wherein a middle portion of the stent provides an outward radial force that is greater than outward radial forces provided by the distal and proximal ends.

15. The device of claim 1, wherein the plurality of cells comprises diamond-shaped cells and parallelogram-shaped cells, the diamond-shaped cells disposed between the parallelogram-shaped cells and the handle, and the handle extending distally from nodes of the plurality of nodes that form the diamond-shaped cells.

16. The device of claim 15, wherein the diamond-shaped cells are configured to distribute tension forces on the stent to facilitate collapse of the stent when the handle is pulled in the axial direction.

17. A device configured to maintain patency of a prostatic urethra, the device comprising:
a stent comprising:
a proximal end;
a distal end;
a passageway between the proximal and distal ends, the passageway configured to facilitate a flow of a bodily fluid from the proximal end to the distal end when the stent is implanted in a prostatic urethra of a patient;
a peripheral wall disposed about the passageway, the peripheral wall comprising a plurality of struts and a plurality of nodes coupled to each other to form a plurality of cells, the plurality of cells comprising diamond-shaped cells and parallelogram-shaped cells; and
a handle formed from a most distal strut of the plurality of struts, wherein the handle is biased to a first position such that the handle does not impede flow of the bodily fluid through the passageway when the stent is implanted in the prostatic urethra of the patient, wherein the handle is further configured to engage a wall of the prostatic urethra, wherein the handle is further configured to extend distally from distal-most nodes of the plurality of nodes forming the diamond-shaped cells, wherein the diamond-shaped cells are disposed between the handle and the parallelogram-shaped cells, wherein the handle is further configured to extend in a distal direction beyond a most distal cell of the plurality of cells when the stent is expanded, and wherein while biased to the first position, a portion of the handle extends in a direction perpendicular to a longitudinal axis of the stent;
wherein the stent is configured to expand from a compressed configuration to an expanded configuration within the prostatic urethra; and
wherein the handle is configured to be deflected, when pulled in the distal direction, from the first position to a second position, wherein the second position is closer to a central longitudinal axis of the stent compared to the first position.

18. The device of claim 17, wherein the diamond-shaped cells are configured to distribute tension forces on the stent to facilitate collapse when the handle is pulled in the axial direction.

19. The device of claim 17, wherein distal parallelogram-shaped cells of the parallelogram-shaped cells share struts of the plurality of struts forming the diamond-shaped cells.

20. The device of claim 17, wherein the handle comprises a divot configured to engage with a capture device for loading the stent into a working lumen of a delivery device, and wherein portions of the strut on opposite sides of the divot are substantially colinear and orthogonal to both the longitudinal axis of the stent and the portion of the handle extending in the direction perpendicular to the longitudinal axis of the stent.

21. A method of loading a stent into a working lumen of a delivery device, the method comprising:
coupling a handle formed from a most distal strut of a plurality of struts of a stent to a capture device, the handle biased to a first position that is coplanar with a peripheral wall of the stent when viewed from an axial direction, wherein the handle is configured to extend in a distal direction beyond a most distal cell of a plurality of cells of the stent when the stent is expanded from a compressed configuration to an expanded configuration within a prostatic urethra, and wherein while biased to the first position, a portion of the handle extends in a direction perpendicular to a longitudinal axis of the stent;
pulling the handle with the capture device in the distal direction to deflect the handle to a second position closer to a central longitudinal axis of the stent compared to the first position; and
retracting the stent by pulling the handle with the capture device into a working lumen of a delivery device such that the stent compresses to a diameter of the working lumen.

22. The method of claim 21, wherein the handle comprises a divot configured to engage with the capture device for loading the stent into a working lumen of a delivery device, and wherein portions of the strut on opposite sides of the divot are substantially colinear and orthogonal to both the longitudinal axis of the stent and the portion of the handle extending in the direction perpendicular to the longitudinal axis of the stent.

* * * * *